(12) United States Patent
Clark et al.

(10) Patent No.: US 6,821,971 B2
(45) Date of Patent: Nov. 23, 2004

(54) FUSED PYRAZOLONE COMPOUNDS WHICH INHIBIT THE RELEASE OF INFLAMMATORY CYTOKINES

(75) Inventors: Michael Philip Clark, Loveland, OH (US); Matthew John Laufersweiler, Cincinnati, OH (US); Jane Far-Jine Djung, Mason, OH (US); Biswanath De, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 74 days.

(21) Appl. No.: 10/245,927

(22) Filed: Sep. 18, 2002

(65) Prior Publication Data

US 2003/0105084 A1 Jun. 5, 2003

Related U.S. Application Data

(60) Provisional application No. 60/323,625, filed on Sep. 20, 2001.

(51) Int. Cl.[7] .................. C07D 487/04; A61K 31/506
(52) U.S. Cl. .................. 514/235.8; 514/236.5; 514/274; 514/275; 544/122; 544/123; 544/296; 544/316; 544/31; 544/332
(58) Field of Search ............... 544/122, 123, 544/316, 296, 331, 332; 514/235.8, 274, 236.5, 275

(56) References Cited

U.S. PATENT DOCUMENTS

| | | | |
|---|---|---|---|
| 3,222,366 A | 12/1965 | Wagner-Jauregg et al. | 260/250 |
| 2003/0134867 A1 * | 7/2003 | Clark et al. | 514/275 |

FOREIGN PATENT DOCUMENTS

| | | |
|---|---|---|
| CH | 529153 A | 10/1972 |

OTHER PUBLICATIONS

Holzheimer, PubMed Abstract (J. Chemother. 13 Spec. No. 1(1):159–72), Nov. 2001.*
van Deventer, PubMed Abstract (Intensive Care Med. 26 Suppl. 1:S98–102), 2000.*
Green et al., PubMed Abstract (Immunol. Rev. 169:11–22), Jun. 1999.*
Rasmussen, PubMed Abstract (Dan Med Bull. 47(2):94–114), Apr. 2000.*
Aleman et al., PubMed Abstract (Antivir Ther. 4(2):109–15), 1999.*

* cited by examiner

*Primary Examiner*—Deepak Rao
(74) *Attorney, Agent, or Firm*—Richard S. Echler, Sr.

(57) ABSTRACT

The present invention relates to compound which are capable of preventing the extracellular release of inflammatory cytokines, said compounds, including all enantiomeric and diasteriomeric forms and pharmaceutically acceptable salts thereof, have the formula:

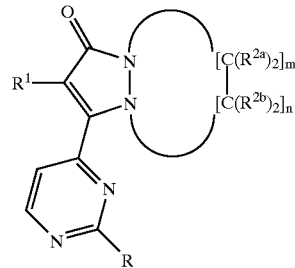

wherein R comprises ethers or amines;

$R^1$ is:
a) substituted or unsubstituted aryl; or
b) substituted or unsubstituted heteroaryl;
$R^{2a}$ and $R^{2b}$ units are each independently hydrogen, ethers, amines, amides, carboxylates, or said units can form a double bond, a carbonyl, or $R^{2a}$ and $R^{2b}$ can be taken together to form a substituted or unsubstituted ring comprising from 4 to 8 atoms, said ring selected from the group consisting of:
i) carbocyclic;
ii) heterocyclic;
iii) aryl;
iv) heteroaryl;
v) bicyclic; and
vi) heterobicyclic.

20 Claims, No Drawings

FUSED PYRAZOLONE COMPOUNDS WHICH INHIBIT THE RELEASE OF INFLAMMATORY CYTOKINES

CROSS REFERENCE TO RELATED APPLICATIONS

This application claims priority under Title 35, United States Code 119(e) from Provisional Application Ser. No. 60/323,625, filed Sep. 20, 2001.

FIELD OF THE INVENTION

The present invention relates to compounds which inhibit the extracellular release of inflammatory cytokines, said cytokines responsible for one or more human or higher mammalian disease states. The present invention further relates to compositions comprising said compounds and method for preventing, abating, or otherwise controlling enzymes which are understood to be the active components responsible for the herein described disease states.

BACKGROUND OF THE INVENTION

Interleukin-1 (IL-1) and Tumor Necrosis Factor-α (TNF-α) are among the important biological substances known collectively as "cytokines." These molecules are understood to mediate the inflammatory response associated with the immunological recognition of infectious agents.

These pro-inflammatory cytokines are suggested as an important mediators in many disease states or syndromes, inter alia, rheumatoid arthritis, osteoarthritis, inflammatory bowel disease (IBS), septic shock, cardiopulmonary dysfunction, acute respiratory disease, cachexia, and therefore responsible for the progression and manifestation of human disease states.

There is therefore a long felt need for compounds and pharmaceutical compositions which comprise compounds, which can block, abate, control, mitigate, or prevent the release of cytokines from cells which produce them

SUMMARY OF THE INVENTION

The present invention meets the aforementioned needs in that it has been surprisingly found that certain [5,6] and [5,6,6] fused ring pyrazolones and derivatives thereof are effective for inhibiting release of inflammatory cytokines, inter alia, interleukin-1 (IL-1) and tumor necrosis factor (TNF) from cells and thereby preventing, abating, or otherwise controlling enzymes which are proposed to be the active components responsible for the herein described disease states.

The first aspect of the present invention relates to compounds, including all enantiomeric and diasteriomeric forms and pharmaceutically acceptable salts thereof, said compounds having the formula:

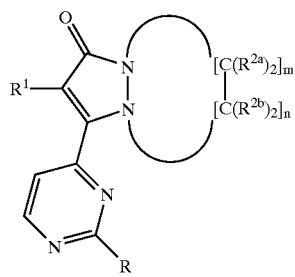

wherein R is:
a) hydrogen;
b) —O(CH$_2$)$_k$R$^3$; or
c) —NR$^{4a}$R$^{4b}$;

R$^3$ is substituted or unsubstituted C$_1$–C$_4$ alkyl, substituted or unsubstituted cyclic hydrocarbyl, substituted or unsubstituted heterocyclyl, substituted or unsubstituted aryl, substituted or unsubstituted heteroaryl; the index k is from 0 to 5;

R$^{4a}$ and R$^{4b}$ are each independently:
a) hydrogen; or
b) —[C(R$^{5a}$R$^{5b}$)]$_x$R$^6$;

each R$^{5a}$ and R$^{5b}$ are independently hydrogen, —OR$^7$, —N(R$^7$)$_2$, —CO$_2$R$^7$, —CON(R$^7$)$_2$; C$_1$–C$_4$ linear, branched, or cyclic alkyl, and mixtures thereof; R$^6$ is hydrogen, —OR$^7$, —N(R$^7$)$_2$, —CO$_2$R$^7$, —CON(R$^7$)$_2$; substituted or unsubstituted C$_1$–C$_4$ alkyl, substituted or unsubstituted aryl, or substituted or unsubstituted heteroaryl; R$^7$ is hydrogen, a water-soluble cation, C$_1$–C$_4$ alkyl, or substituted or unsubstituted aryl; the index x is from 0 to 5;

R$^1$ is:
a) substituted or unsubstituted aryl; or
b) substituted or unsubstituted heteroaryl;

R$^{2a}$ and R$^{2b}$ units are each independently selected from the group consisting of:
a) hydrogen;
b) —O(CH$_2$)$_j$R$^8$;
c) —(CH$_2$)$_j$NR$^{9a}$R$^{9b}$;
d) —(CH$_2$)$_j$CO$_2$R$^{10}$;
e) —(CH$_2$)$_j$OCO$_2$R$^{10}$
f) —(CH$_2$)$_j$CON(R$^{10}$)$_2$;
g) two R$^{2a}$ or two R$^{2b}$ units from the same carbon atom can be taken together to form a carbonyl unit;
h) one R$^{2a}$ and one R$^{2b}$ are taken together to form a double bond;
i) one R$^{2a}$ and one R$^{2b}$ are taken together to form a substituted or unsubstituted ring comprising from 4 to 8 atoms, said ring selected from the group consisting of:
  i) carbocyclic;
  ii) heterocyclic;
  iii) aryl;
  iv) heteroaryl;
  v) bicyclic; and
  vi) heterobicyclic;
j) and mixtures thereof;

R$^8$, R$^{9a}$, R$^{9b}$, and R$^{10}$ are each independently hydrogen, C$_1$–C$_4$ alkyl, and mixtures thereof; R$^{9a}$ and R$^{9b}$ can be taken together to form a carbocyclic or heterocyclic ring comprising from 3 to 7 atoms; two R$^{10}$ units can be take together to form a carbocyclic or heterocyclic ring comprising from 3 to 7 atoms; j is an index from 0 to 5; m is an index from 1 to 5, n is an index from 1 to 5; m+n=from 2 to 6.

Another aspect of the present invention relates to pharmaceutical compositions which can deliver the compounds of the present invention to a human or higher mammal, said compositions comprising:

a) an effective amount of one or more of the compounds according to the present invention; and b) one or more pharmaceutically acceptable excipients.

A further aspect of the present invention relates to methods for controlling one or more inflammatory cytokine mediated or inflammatory cytokine modulated mammalian diseases or conditions, said method comprising the step of administering to a human or higher mammal and effective amount of a composition comprising one or more of the compounds according to the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The present invention relates to compounds which are capable of mediating, controlling or otherwise inhibiting the extracellular release of certain cytokines, especially inflammatory cytokines, said cytokines playing a role in the stimulation, cause or manifestation of a wide variety of diseases, disease states, or syndromes.

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various unsubstituted non-heterocyclic hydrocarbyl units include pentyl, 3-ethyloctanyl, 1,3-dimethylphenyl, cyclohexyl, cis-3-hexyl, 7,7-dimethylbicyclo[2.2.1]-heptan-1-yl, and naphth-2-yl.

Included within the definition of "hydrocarbyl" are the aromatic (aryl) and non-aromatic carbocyclic rings, non-limiting examples of which include cyclopropyl, cyclobutanyl, cyclopentanyl, cyclohexane, cyclohexenyl, cycloheptanyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl (norboranyl), bicyclo-[0.2.4]-octanyl (caryophyllenyl), spiropentanyl, diclyclopentanespiranyl, decalinyl, phenyl, benzyl, naphthyl, indenyl, 2H-indenyl, azulenyl, phenanthryl, anthryl, fluorenyl, acenaphthylenyl, 1,2,3,4-tetrahydronaphthalenyl, and the like.

The term "heterocycle" includes both aromatic (heteroaryl) and non-aromatic heterocyclic rings non-limiting examples of which include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl, 2H-indenyl, benzofuranyl, isobenzofuranyl, indolyl, 3H-indolyl, 1H-indolyl, benzoxazolyl, 2H-1-benzopyranyl, quinolinyl, isoquinolinyl, quinazolinyl, 2H-1,4-benzoxazinyl, pyrrolidinyl, pyrrolinyl, quinoxalinyl, furanyl, thiophenyl, benzimidazolyl, and the like each of which can be substituted or unsubstituted.

An example of a unit defined by the term "alkylenearyl" is a benzyl unit having the formula:

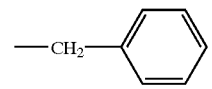

whereas an example of a unit defined by the term "alkyleneheteroaryl" is a 2-picolyl unit having the formula:

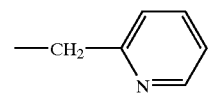

The term "substituted" is used throughout the specification. The term "substituted" is defined herein as "encompassing moieties or units which can replace a hydrogen atom, two hydrogen atoms, or three hydrogen atoms of a hydrocarbyl moiety. Also substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. An epoxide unit is an example of a substituted unit which requires replacement of a hydrogen atom on adjacent carbons. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit." The following are non-limiting examples of units which can serve as a replacement for hydrogen atoms when a hydrocarbyl unit is described as "substituted."

i) $—[C(R^{12})_2]_p(CH=CH)_qR^{12}$; wherein p is from 0 to 12; q is from 0 to 12;
ii) $—C(Z)R^{12}$;
iii) $—C(Z)_2R^{12}$;
iv) $—C(Z)CH=CH_2$;
v) $—C(Z)N(R^{12})_2$;
vi) $—C(Z)NR^{12}N(R^{12})_2$;
vii) $—CN$;
viii) $—CNO$;
ix) $—CF_3, —CCl_3, —CBr_3$;
Z) $—N(R^{12})_2$;
xi) $—NR^{12}CN$;
xii) $—NR^{12}C(Z)R^{12}$;
xiii) $—NR^{12}C(Z)N(R^{12})_2$;
xiv) $—NHN(R^{12})_2$;
xv) $—NHOR^{12}$;

xvi) —NCS;
xvii) —NO$_2$;
xviii) —OR$^{12}$;
xix) —OCN;
xx) —OCF$_3$, —OCCl$_3$, —OCBr$_3$;
xxi) —F, —Cl, —Br, —I, and mixtures thereof;
xxii) —SCN;
xxiii) —SO$_3$M;
xxiv) —OSO$_3$M;
xxv) —SO$_2$N(R$^{12}$)$_2$;
xxvi) —SO$_2$R$^{12}$;
xxvii) —P(O)H$_2$;
xxviii) —PO$_2$;
xxix) —P(O)(OH)$_2$;
xxx) and mixtures thereof;
wherein R$^{12}$ is hydrogen, substituted or unsubstituted C$_1$–C$_{20}$ linear, branched, or cyclic alkyl, C$_6$–C$_{20}$ aryl, C$_7$–C$_{20}$ alkylenearyl, and mixtures thereof; M is hydrogen, or a salt forming cation; Z is =O, =S, =NR$^{12}$, and mixtures thereof. Suitable salt forming cations include, sodium, lithium, potassium, calcium, magnesium, ammonium, and the like.

The first aspect of the present invention as a whole, relates to novel compounds suitable for inhibiting release of inflammatory cytokines, said compounds having the formula:

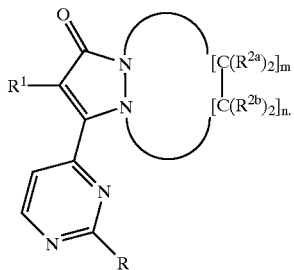

R is a substituent at the 2-position of the pyrimidin-4-yl portion of the general scaffold, said R unit is:

a) an ether having the formula —O[CH$_2$]$_k$R$^3$; or
b) a primary or secondary amino unit having the formula —NR$^{4a}$R$^4$b;

wherein R$^3$ is substituted or unsubstituted C$_1$–C$_4$ alkyl, substituted or unsubstituted cyclic hydrocarbyl, substituted or unsubstituted heterocyclyl, substituted or unsubstituted aryl, substituted or unsubstituted heteroaryl; the index k is from 0 to 5.

The following are the various aspects of R units according to the present invention wherein R is an ether having the formula —O[CH$_2$]$_k$R$^3$. However, the formulator is not limited to the herein exemplified iterations and examples.

A) R units encompassing ethers having the formula —OR$^3$ (the index k equal to 0) and R$^3$ is substituted or unsubstituted aryl.
  i) One iteration of this aspect of R comprises ethers having the formula —OR$^3$ and R$^3$ is substituted or unsubstituted aryl. This iteration includes the following non-limiting example of R: phenoxy, 2-fluorophenoxy, 3-fluorophenoxy, 4-fluorophenoxy, 2,4-difluorophenoxy, 3-trifluoromethyl-phenoxy, 4-trifluoromethylphenoxy, 2,4-trifluoromethyl phenoxy, and the like.
  ii) Another iteration of this aspect of R comprises ethers having the formula —OR$^3$ and R$^3$ is substituted or unsubstituted aryl. This iteration includes the following non-limiting examples: 2-methylphenoxy, 3-methylphenoxy, 4-methylphenoxy, 2,4-dimethylphenoxy, 2-cyanophenoxy, 3-cyanophenoxy, 4-cyanophenoxy, 4-ethylphenoxy, and the like.
  iii) A further iteration of this aspect of R comprises ethers having the formula —OR$^3$ and R$^3$ is substituted or unsubstituted aryl. This iteration includes the following non-limiting examples: (2-methyoxy)phenoxy, (3-methoxy)phenoxy, (4-methoxy)phenoxy, 3-[(N-acetyl)amino]phenoxy, 3-benzo[1,3]dioxol-5-yl, and the like.

B) R units encompassing ethers having the formula —OR$^3$ (the index k equal to 0) and R$^3$ is substituted or unsubstituted heteroaryl.
  i) A first iteration of this aspect of R comprises ethers having the formula —OR$^3$ and R$^3$ is unsubstituted heteroaryl. This iteration includes the following non-limiting examples: pyrimidin-2-yl, pyrimidin-4-yl, pyridin-2-yl, pyridin-3-yl, pyridin-4-yl, and the like.
  ii) A second iteration of this aspect of R comprises ethers having the formula —OR$^3$ and R$^3$ is substituted heteroaryl. This iteration includes the following non-limiting examples: 2-aminopyrimidin-4-yl, and the like.

C) R units encompassing ethers having the formula —OCH$_2$R$^3$ (the index k equal to 1) and R$^3$ is substituted or unsubstituted aryl.
  i) A first iteration of this aspect of R comprises ethers having the formula —OCH$_2$R$^3$ and R$^3$ is substituted or unsubstituted heteroaryl. This iteration includes the following non-limiting examples: pyrimidin-2-yl, pyrimidin-4-yl, 2-aminopyrimidin-4-yl, 4-aminopyrimidin-6-yl, pyridin-2-yl, pyridin-3-yl, pyridin-4-yl, and the like.
  ii) A second iteration of this aspect of R wherein R is an ether having the formula —OCH$_2$R$^3$ and R$^3$ is substituted or unsubstituted alkyleneheteroaryl. This iteration includes the following non-limiting examples: pyridin-3-ylethyl, (2-methyl-2-pyridin-3-yl)ethyl, and the like.

D) R units encompassing ethers having the formula —OR$^3$ (the index k equal to 1) and R$^3$ is substituted or unsubstituted C$_1$–C$_4$ alkyl.
  i) A first iteration of this aspect of R is an ether having the formula —OR$^3$ and R$^3$ is unsubstituted C$_1$–C$_4$ linear, branched, or cyclic alkyl. This iteration includes the following non-limiting examples: methyl, ethyl, isopropyl, (S)-1-methypropyl, and the like.
  ii) A second iteration of this aspect of R is an ether having the formula —OR$^3$ and R$^3$ is a substituted C$_1$–C$_4$ linear, branched, or cyclic alkyl. This iteration includes the following non-limiting examples: 2-methoxyethyl, (S)-1-methy-3-methoxypropyl, and the like.

The following are the various aspects of R units according to the present invention wherein R is an amine having the formula —NR$^{4a}$R$^{4b}$, R$^{4a}$ and R$^{4b}$ are each independently:
  a) hydrogen; or
  b) —[C(R$^{5a}$R$^{5b}$)]$_x$R$^6$;
each R$^{5a}$ and R$^{5b}$ are independently hydrogen, —OR$^7$, —N(R$^7$)$_2$, —CO$_2$R$^7$, —CON(R$^7$)$_2$, C$_1$–C$_4$ linear, branched, or cyclic alkyl, and mixtures thereof; R$^6$ is hydrogen, —OR$^7$, —N(R$^7$)$_2$, —CO$_2$R$^7$, —CON(R$^7$)$_2$; substituted or unsubstituted C$_1$–C$_4$ alkyl, substituted or unsubstituted aryl, or substituted or unsubstituted heteroaryl; R$^7$ is hydrogen, a water-soluble cation, C$_1$–C$_4$ alkyl, or substituted or unsubstituted aryl; the index x is from 0 to 5. However, the formulator is not limited to the herein exemplified iterations and examples.

A) R units encompassing chiral amino groups wherein $R^{4a}$ is hydrogen, $R^{5a}$ is hydrogen and $R^{5b}$ is methyl, said units having the formula:

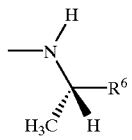

and the indicated stereochemistry.

i) A first iteration of this aspect of R is an amine comprising an $R^6$ which is substituted or unsubstituted phenyl. This iteration includes the following non-limiting examples: (S)-1-methyl-1-phenylmethylamino, (S)-1-methyl-1-(4-fluorophenyl)methylamino, (S)-1-methyl-1-(4-methylphenyl)methyl-amino, (S)-1-methyl-1-(4-methoxyphenyl)methylamino, (S)-1-methyl-1-(2-aminophenyl)methylamino, (S)-1-methyl-1-(4-aminophenyl)methylamino, and the like.

ii) A second iteration of this aspect of R is an amine comprising an $R^6$ which is substituted or unsubstituted heteroaryl. This iteration includes the following non-limiting examples: (S)-1-methyl-1-(pyridin-2-yl)methylamino, (S)-1-methyl-1-(pyridin-3-yl)methylamino, (S)-1-methyl-1-(pyridin-4-yl)methylamino, (S)-1-methyl-1-(furan-2-yl)methylamino, (S)-1-methyl-1-(3-benzo[1,3]dioxol-5-yl)methylamino, and the like.

iii) A third iteration of this aspect of R is an amine comprising an $R^6$ which is $C_1$–$C_4$ substituted or unsubstituted alkyl. This iteration includes the following non-limiting examples: (S)-1-methylpropylamino, (S)-1-methyl-2-(methoxy)ethylamino.

B) R units encompassing chiral amino groups wherein $R^{4a}$ is hydrogen, $R^{5a}$ and $R^{5b}$ are each $C_1$–$C_4$ alkyl, said units having the formula:

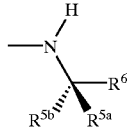

and the indicated stereochemistry when $R^{5a}$, $R^{5b}$ and $R^6$ are not the same.

i) A first iteration of this aspect of R is an amine which does not have a chiral center, non-limiting examples of which includes 1,1-dimethylethylamine, 1,1-dimethylbenzylamine and the like.

ii) A second iteration of this aspect of R is an amine comprising an $R^6$ which is substituted or unsubstituted $C_1$–$C_4$ alkyl. This iteration includes the following non-limiting examples: (S)-1-methyl-2-hydroxy-2-methylpropylamine, (S)-1-methyl-2-hydroxy-2-methylbutylamine, and the like.

C) R units encompassing alkylenearyl amines wherein $R^{4a}$ is hydrogen, both $R^{5a}$ and $R^{5b}$ of $R^{4b}$ are hydrogen, $R^6$ is substituted or unsubstituted aryl, said unit having the formula:

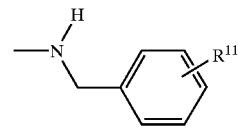

wherein $R^{11}$ is hydrogen or a "substituted unit" as defined herein above.

i) A first iteration of this aspect comprises the following non-limiting examples of R units: benzylamino, (2-aminophenyl)methylamino; (4-fluorophenyl)methylamino, (4-methoxyphenyl)methylamino; (4-propanesulfonylphenyl)methylamino; and the like.

ii) A second iteration of this aspect comprises the following non-limiting examples of R units: (2-methylphenyl)methylamino; (3-methylphenyl)-methylamino; (4-methylphenyl)methylamino; and the like.

D) R units encompassing amines wherein $R^{4a}$ is hydrogen, $R^{4b}$ comprises $R^{5a}$ equal to hydrogen and $R^{5b}$ equal to —$CO_2R^7$ or —$CON(R^7)_2$; said unit having the formula:

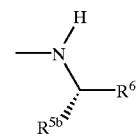

i) A first iteration of this aspect of R is an amine comprising an $R^6$ which is substituted or unsubstituted phenyl. This iteration includes the following non-limiting examples:

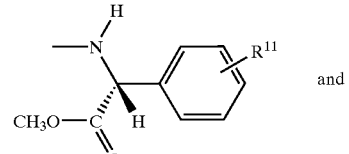

and

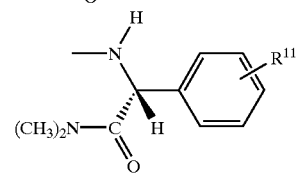

wherein $R^{11}$ is hydrogen or a "substitute" as defined herein above.

ii) A second iteration of this aspect of R is an amine comprising an $R^6$ which is substituted or unsubstituted alkyl. This iteration includes the following non-limiting examples:

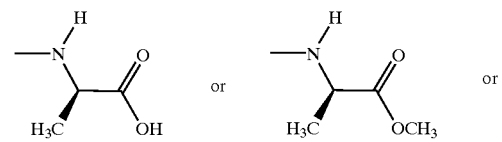

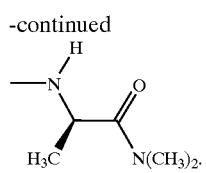

$R^1$ units are selected from:
a) substituted or unsubstituted aryl; or
b) substituted or unsubstituted heteroaryl.

The first aspect of $R^1$ units encompasses halogen substituted phenyl units, non-limiting examples of which include 4-fluorophenyl, 2,4-difluorophenyl, 4-chlorophenyl, and the like. $R^{2a}$ and $R^{2b}$ units are each independently selected from the group consisting of:
a) hydrogen;
b) —O(CH$_2$)$_j$R$^8$;
c) —(CH$_2$)$_j$NR$^{9a}$R$^{9b}$;
d) —(CH$_2$)$_j$CO$_2$R$^{10}$;
e) —(CH$_2$)$_j$OCO$_2$R$^{10}$
f) —(CH$_2$)$_j$CON(R$^{10}$)$_2$;
g) two $R^{2a}$ or two $R^{2b}$ units from the same carbon atom can be taken together to form a carbonyl unit;
h) one $R^{2a}$ and one $R^{2b}$ are taken together to form a double bond;
i) one $R^{2a}$ and one $R^{2b}$ are taken together to form a substituted or unsubstituted ring comprising from 4 to 8 atoms, said ring selected from the group consisting of:
  i) carbocyclic;
  ii) heterocyclic;
  iii) aryl;
  iv) heteroaryl;
  v) bicyclic; and
  vi) heterobicyclic;
j) and mixtures thereof;

$R^8$, $R^{9a}$, $R^{9b}$, and $R^{10}$ are each independently hydrogen, $C_1$-$C_4$ alkyl, and mixtures thereof; $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5.

[5,6]-Fused Rings Systems

A first aspect of the present invention relates to ring scaffolds wherein the indices m and n are each equal to 2, thereby comprising a 2-($R^1$-substituted)-3-(2-R-substituted-pyrimidin-4-yl)-5,6,7,8-tetrahydro-pyrazolo[1,2-a]pyridazin-1-one scaffolds having the formula:

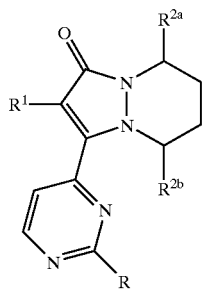

wherein the $R^{2a}$ and $R^{2b}$ units are each independently hydrogen, —(CH$_2$)$_j$CO$_2$R$^{10}$, —(CH$_2$)$_j$CON(R$^{10}$)$_2$, and mixtures thereof.

Iterations of this scaffold include the core scaffold having the formula:

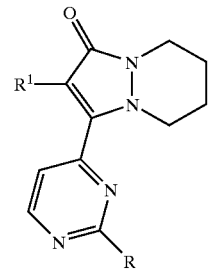

the 5,6,7,8-tetrahydro-pyrazolo[1,2-a]-pyridazin-1-one 8-position esters and amides having the formula:

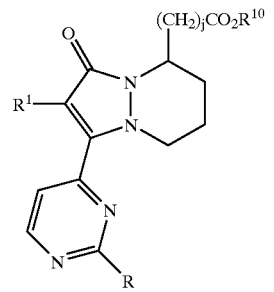

and

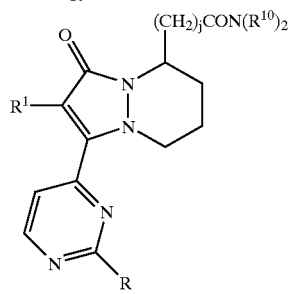

as well as the 5,6,7,8-tetrahydro-pyrazolo[1,2-a]-pyridazin-1-one 5-position esters and amides having the formula:

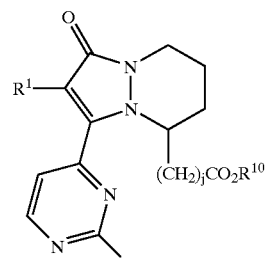

and

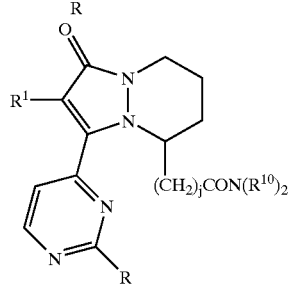

A second aspect of the present invention as it relates to $R^{2a}$ and $R^{2b}$ units, comprises 2-($R^1$-substituted)-3-(2-R- substituted-pyrimidin-4-yl)-5,6,7,8-tetrahydro-pyrazolo[1,2-a]pyridazin-1-one scaffolds having the formula:

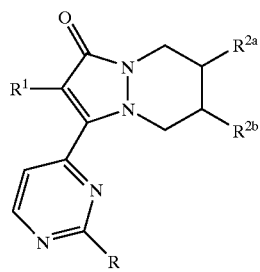

wherein each of the $R^{2a}$ and $R^{2b}$ units is independently selected form the group consisting of:

a) hydrogen;
b) —O(CH$_2$)$_j$R$^8$; and
c) —(CH$_2$)$_j$NR$^{9a}$R$^{9b}$.

Iterations of this aspect include 6-hydroxy-2-(R$^1$-substituted)-3-(2-R-substituted-pyrimidin-4-yl)-5,6,7,8-tetrahydro-pyrazolo[1,2-a]-pyridazin-1-ones, 7-hydroxy-2-(R$^1$-substituted)-3-(2-R-substituted-pyrimidin-4-yl)-5,6,7,8-tetrahydro-pyrazolo[1,2-a]-pyridazin-1-ones, 6-(dimethylamino)-2-(R$^1$-substituted)-3-(2-R-substituted-pyrimidin-4-yl)-5,6,7,8-tetrahydro-pyrazolo[1,2-a]-pyridazin-1-ones, 6-morpholino-2-(R$^1$-substituted)-3-(2-R-substituted-pyrimidin-4-yl)-5,6,7,8-tetrahydro-pyrazolo[1,2-a]-pyridazin-1-ones A third aspect of the present invention as it relates to $R^{2a}$ and $R^{2b}$ units, comprises scaffolds wherein two adjacent $R^{2a}$ and $R^{2b}$ units are taken together to form a double bond, for example a 2-(R$^1$-substituted)-3-(2-R-substituted-pyrimidin-4-yl)-5,8-dihydro-pyrazolo[1,2-a]-pyridazin-1-one scaffolds having the formula:

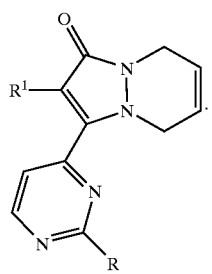

[5,6,X]-Fused Rings Systems

The present invention also relates to [5,6,X]-fused ring systems wherein X is a ring formed when one $R^{2a}$ and one $R^{2b}$ are taken together to form a substituted or unsubstituted ring comprising from 4 to 8 atoms. The rings formed are selected from the group consisting of:

i) carbocyclic;
ii) heterocyclic;
iii) aryl;
iv) heteroaryl;
v) bicyclic; and
vi) heterobicyclic;

A first embodiment of this aspect relates to ring systems wherein one $R^{2a}$ and one $R^{2b}$ are taken together to form a 6-membered aryl ring, inter alia, the [5,6,6]-fused rings system; 2-(R$^1$-substituted)-3-(2-R-substituted-pyrimidin-4-yl)-5,10-dihydro-pyrazolo[1,2-b]phthalazin-1-one having the formula:

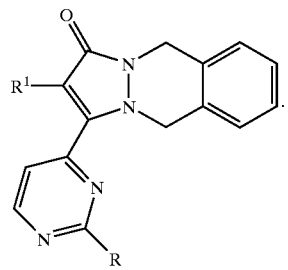

Iterations of this aspect include analogs which are substituted on the C-ring, for example compounds having the formula:

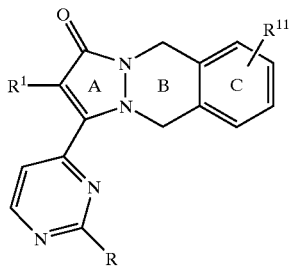

wherein R$^{12}$ is a substituent as described herein above. A non-limiting example of the [5,6,6] ring scaffolds of the present invention are the 2-(R$^1$-substituted)-3-(2-R-substituted-pyrimidin-4-yl)-5,10-dihydro-pyrazolo[1,2-b]phthalazin-1-one ring scaffolds, for example the compound having the formula:

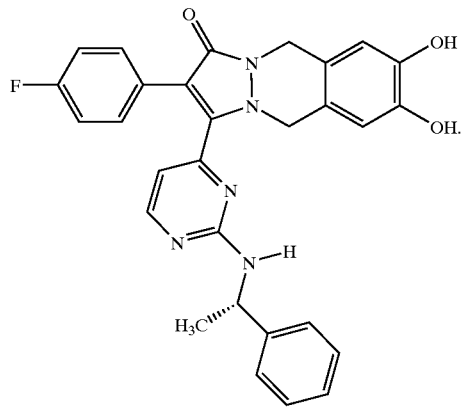

The first aspect of Category I analogs capable of inhibiting release of inflammatory cytokines according to the present invention relates to compounds comprising a 5,10-dihydro-pyrazolo[1,2-b]phthalazine-1-one scaffold having the formula:

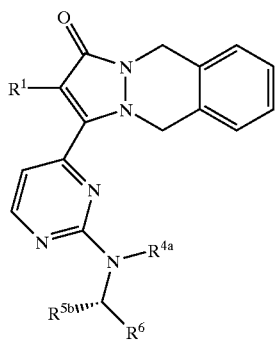

wherein R units are amines having the formula —NH[CHR$^5$]R$^6$, and R$^1$, R$^{4a}$, R$^5$, and R$^6$ are described herein below in Table I. The stereochemistry of R$^{5b}$ is the configuration shown when R$^{5b}$ is not hydrogen.

TABLE I

| No. | R$^1$ | R$^{4a}$ | R$^{5b}$ | R$^6$ |
|---|---|---|---|---|
| 1 | 4-fluorophenyl | H | H | phenyl |
| 2 | 4-fluorophenyl | H | H | 4-fluorophenyl |
| 3 | 4-fluorophenyl | H | H | 2-aminophenyl |
| 4 | 4-fluorophenyl | H | H | 2-methylphenyl |
| 5 | 4-fluorophenyl | H | H | 4-methylphenyl |
| 6 | 4-fluorophenyl | H | H | 4-methoxyphenyl |
| 7 | 4-fluorophenyl | H | H | 4-(propanesulfonyl)phenyl |
| 8 | 4-fluorophenyl | H | H | 3-benzo[1,3]dioxol-5-yl |
| 9 | 4-fluorophenyl | H | H | pyridin-2-yl |
| 10 | 4-fluorophenyl | H | H | pyridin-3-yl |
| 11 | 4-fluorophenyl | H | H | H |
| 12 | 4-fluorophenyl | H | H | methyl |
| 13 | 4-fluorophenyl | H | H | ethyl |
| 14 | 4-fluorophenyl | H | H | vinyl |
| 15 | 4-fluorophenyl | H | H | cyclopropyl |
| 16 | 4-fluorophenyl | H | H | cyclohexyl |
| 17 | 4-fluorophenyl | H | H | methoxymethyl |
| 18 | 4-fluorophenyl | H | H | methoxyethyl |
| 19 | 4-fluorophenyl | H | H | 1-hydroxy-1-methylethyl |
| 20 | 4-fluorophenyl | H | H | —CO$_2$H |
| 21 | 4-fluorophenyl | H | methyl | phenyl |
| 22 | 4-fluorophenyl | H | methyl | 4-fluorophenyl |
| 23 | 4-fluorophenyl | H | methyl | 2-aminophenyl |
| 24 | 4-fluorophenyl | H | methyl | 2-methylphenyl |
| 25 | 4-fluorophenyl | H | methyl | 4-methylphenyl |
| 26 | 4-fluorophenyl | H | methyl | 4-methoxyphenyl |
| 27 | 4-fluorophenyl | H | methyl | 4-(propanesulfonyl)phenyl |
| 28 | 4-fluorophenyl | H | methyl | 3-benzo[1,3]dioxol-5-yl |
| 29 | 4-fluorophenyl | H | methyl | pyridin-2-yl |
| 30 | 4-fluorophenyl | H | methyl | pyridin-3-yl |
| 31 | 4-fluorophenyl | H | methyl | H |
| 32 | 4-fluorophenyl | H | methyl | methyl |
| 33 | 4-fluorophenyl | H | methyl | ethyl |
| 34 | 4-fluorophenyl | H | methyl | vinyl |
| 35 | 4-fluorophenyl | H | methyl | cyclopropyl |
| 36 | 4-fluorophenyl | H | methyl | cyclohexyl |
| 37 | 4-fluorophenyl | H | methyl | methoxymethyl |
| 38 | 4-fluorophenyl | H | methyl | methoxyethyl |
| 39 | 4-fluorophenyl | H | methyl | 1-hydroxy-1-methylethyl |
| 40 | 4-fluorophenyl | H | methyl | —CO$_2$H |
| 41 | 3-trifluoromethylphenyl | H | methyl | phenyl |
| 42 | 3-trifluoromethylphenyl | H | methyl | 4-fluorophenyl |
| 43 | 3-trifluoromethylphenyl | H | methyl | 2-aminophenyl |
| 44 | 3-trifluoromethylphenyl | H | methyl | 2-methylphenyl |
| 45 | 3-trifluoromethylphenyl | H | methyl | 4-methylphenyl |
| 46 | 3-trifluoromethylphenyl | H | methyl | 4-methoxyphenyl |

TABLE I-continued

| No. | R$^1$ | R$^{4a}$ | R$^{5b}$ | R$^6$ |
|---|---|---|---|---|
| 47 | 3-trifluoromethylphenyl | H | methyl | 4-(propanesulfonyl)phenyl |
| 48 | 3-trifluoromethylphenyl | H | methyl | 3-benzo[1,3]dioxol-5-yl |
| 49 | 3-trifluoromethylphenyl | H | methyl | pyridin-2-yl |
| 50 | 3-trifluoromethylphenyl | H | methyl | pyridin-3-yl |
| 51 | 3-trifluoromethylphenyl | H | methyl | H |
| 52 | 3-trifluoromethylphenyl | H | methyl | methyl |
| 53 | 3-trifluoromethylphenyl | H | methyl | ethyl |
| 54 | 3-trifluoromethylphenyl | H | methyl | vinyl |
| 55 | 3-trifluoromethylphenyl | H | methyl | cyclopropyl |
| 56 | 3-trifluoromethylphenyl | H | methyl | cyclohexyl |
| 57 | 3-trifluoromethylphenyl | H | methyl | methoxymethyl |
| 58 | 3-trifluoromethylphenyl | H | methyl | methoxyethyl |
| 59 | 3-trifluoromethylphenyl | H | methyl | 1-hydroxy-1-methylethyl |
| 60 | 3-trifluoromethylphenyl | H | methyl | —CO$_2$H |

The following is a scheme for preparing compounds belonging to the first aspect of Category I according to the present invention. The first stage encompasses utilization of Type I intermediates, for example, intermediate 3 to introduce the selected R$^1$ unit into the assembling scaffold.

General Scheme for Intermediate Type I

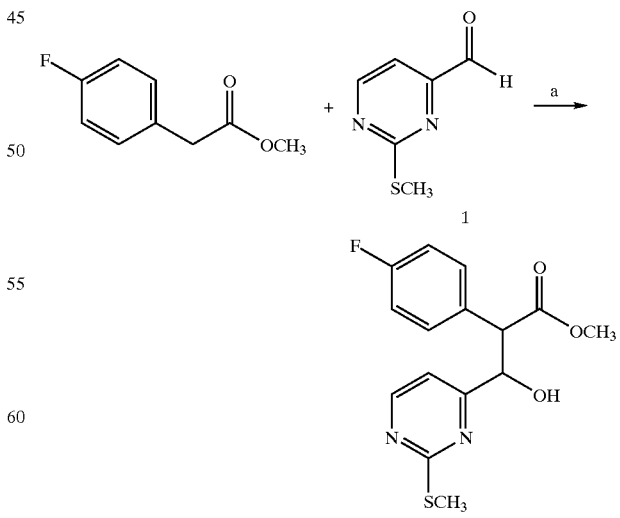

Reagents and conditions: (a) LDA, THF, -78° C., 45 min.

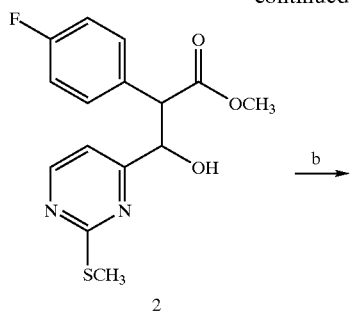

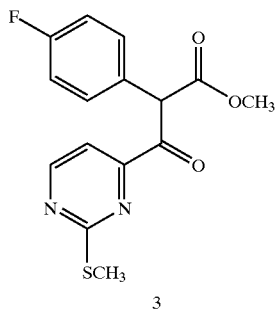

Reagents and conditions: (b) CrO₃, CH₂Cl₂, rt, 16 hr.

EXAMPLE 1

2-(4-Fluorophenyl)-3-(2-methylsulfanyl-pyrimidin-4-yl)-3-oxo-propionic acid methyl ester (3)

The following is a procedure for the preparation of 2-methylsulfanyl-pyrimidine-4-carbaldehyde, 1, adapted from the procedure of H. Bredereck et al., *Chem. Ber.*, 97, pp 3407–3417 (1964) included herein by reference.

To a 12 L 3-neck flask under inert atmosphere is charged N,N-dimethyl-formamide dimethyl acetyl (801 g) and pyruvic aldehyde dimethyl acetal (779 g). The mixture is heated to reflux for 18 hours during which time the temperature decreases from about 109° C. to about 80° C. The solution is cooled and methanol (4 L) is added to dissolve the crude residue. The solution is then cooled to 20° C. and thiourea (892 g, 11.7 mol) is added. After allowing the mixture to stir about 15 minutes, sodium methoxide (741 g, 13.7 mol) is added in 4 equal portions over 1 hour while maintaining the solution temperature in the range of 18–28° C. The mixture is stirred for 5 hours at room temperature, cooled to 20° C., then methyl iodide (2 kg) is added over 1.25 hours while maintaining the reaction temperature in the range of 17–29° C. Stirring is continued for 18 hours at room temperature. The methanol and unreacted methyl iodide is removed by heating the solution at 35° C. @ 40 torr to produce about 4.46 kg of a dark residue which is partitioned between 14 L of water and 5 L of ethyl acetate. The water fraction is extracted a second time with ethyl acetate, the organic layers combined and concentrated in vacuo too afford 685 g of an oil which is purified over silica to 522 g of 4-dimethoxymethyl-2-methylsulfanyl-pyrimidine.

The dimethyl acetal obtained above is then hydrolyzed to the free aldehyde by heating to 60° C. for 3 hours in 1 M HCl. Workup for neutral using ethyl acetate to extract the product affords 347 g crude product which is purified over silica to afford 401 g of 2-methylsulfanyl-pyrimidine-4-carbaldehyde, 1.

Preparation of 2-(4-fluorophenyl)-3-(2-methylsulfanyl-pyrimidin-4-yl)-3-hydroxypropionic acid methyl ester (2): To a cold (−78° C.) solution of lithium diisopropylamide (21.4 mL of 2M solution in THF, 42.8 mmol) in THF (70 mL) is added dropwise a solution of methyl 4-fluorophenyl-acetate (6.0 g, 35.7 mmol) in THF (30 mL). The solution is stirred for 1 hour at −78° C. after which a solution of 2-methylsulfanyl-pyrimidine-4-carbaldehyde, 1, (6.0 g, 39.3 mmol) in THF (30 mL) is added dropwise to the reaction mixture. Stirring is continued for 45 minutes at −78° C. then the reaction is quenched by pouring the reaction solution into aqueous saturated NH₄Cl. The aqueous phase is extracted with ethyl acetate. The organic phases combined, dried (MgSO₄), filtered, and concentrated in vacuo. The crude residue is purified over silica (33% EtOAc/hexanes) to afford 8.7 g (76%) of the desired product as a mixture (1:1) of diastereomers.

Preparation of 2-(4-fluorophenyl)-3-(2-methylsulfanyl-pyrimidin-4-yl)-3-oxo-propionic acid methyl ester (3): To a suspension of CrO₃ in CH₂Cl₂ (300 mL) is added pyridine. The mixture is stirred vigorously for 1 hour at room temp. A solution of the crude 2-(4-fluorophenyl)-3-(2-methylsulfanyl-pyrimidin-4-yl)-3-hydroxypropionic acid methyl ester, 2, prepared above in CH₂Cl₂ (50 mL) is added dropwise to the chromium suspension. The reaction mixture is stirred at room temperature for 16 hours, diluted with ether (1 L) and filtered through a pad of Celite. The filtrate is concentrated in vacuo and the resulting residue is purified over silica (25% EtOAc/hexanes) to afford 3.7 g (43% yield) of the desired product as a yellow solid.

The following example relates to the formation of 6,7-dihydro-5H-pyrazolo[1,2-a]pyrazol-1-one ring systems utilizing pyrazolidine, however the formulator may substitute other cyclic hydrazine reagents to achieve other scaffolds according to the present invention, inter alia, the use of hexahydro-pyridazine to prepare 5,6,7,8-tetrahydro-pyrazolo[1,2-a]pyridazin-1-ones. In the example herein below, intermediate 3, prepared by the method described herein above is use to introduce as R¹ a 4-fluorophenyl unit, however, substitution for this unit can be accomplished during the preparation of the β-ketoester intermediate.

The following scheme illustrates the preparation of Intermediate Type II, for example, intermediate 5, which encompasses scaffold rings B and C.

General Scheme for Intermediate Type II

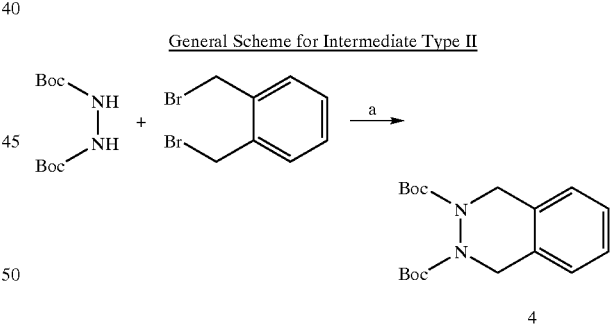

Reagents and conditions: (a) NaH, DMF, 90° C., 3 hr.

Reagents and conditions: (b) SOCl₂, MeOH, rt, 72 hr.

EXAMPLE 2

1,2,3,4-Tetrahydrophthalazine (5)

Preparation of 1,4-dihydrophthalazine-2,3-dicarboxylic acid di-tert-butyl ester (4): To a solution of di-tertbutylhydrazodiformate (3.0 g, 13.0 mmol) in DMF (20 mL) at room temp is added NaH (0.5 g, 13.0 mmol). After stirring 1 hour at room temp, 1,2-bis-bromomethylbenzene (3.4 g, 13.0 mmol) is added to the reaction mixture. After stirring 1 hour at room temperature, another portion of NaH (0.5 g, 13.0 mmol) is added to the reaction mixture. The mixture is then heated to 90° C. for 3 hours, allowed to cool to room temperature and stirring is continued at room temp for 15 hours. The reaction can then be quenched by pouring the reaction solution into aqueous saturated NH$_4$Cl. The aqueous phase is extracted with ether, the organic phase dried (MgSO$_4$), filtered and concentrated in vacuo. The crude residue is purified over silica (5% EtOAc/hexanes) to afford 1.0 g (23% yield) of the desired product as a clear oil.

Preparation of 1,2,3,4-tetrahydrophthalazine (5): 1,4-dihydrophthalazine-2,3-dicarboxylic acid di-tert-butyl ester, 4, (1.0 g, 3 mmol) is dissolved in MeOH (20 mL) and SOCl$_2$ (0.5 mL) added dropwise. After stirring at room temp for 72 hours, the solvent is removed in vacuo to afford 0.6 g of the desired product as white solid.

The following scheme illustrates the assembly of the 3-pyrimidin-4-yl-5,10-dihydro-pyrazolo[1,2-b]phthalazine-1-one scaffold by the convergent step which condenses intermediates 3 and 5. The resulting intermediate is then transformed into the final compound having the selected R unit.

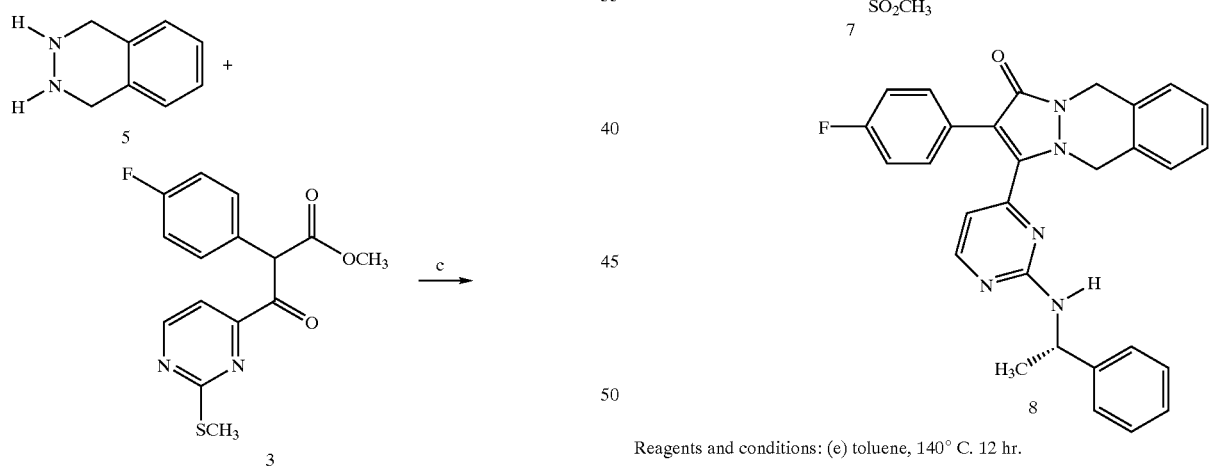

Reagents and conditions: (c) pyridine, reflux 16 hr.

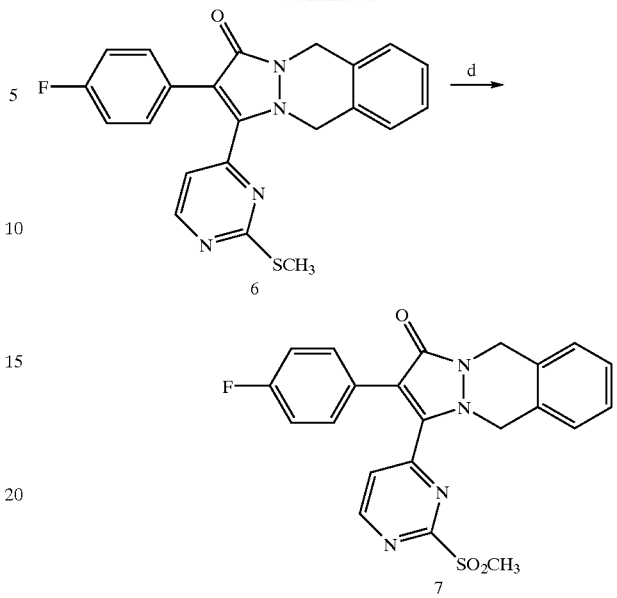

Reagents and conditions: (d) OXONE®, THF/MeOH, rt 2 hr.

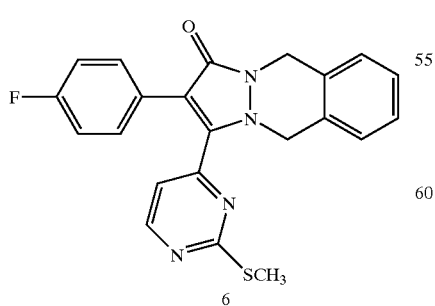

Reagents and conditions: (e) toluene, 140° C. 12 hr.

EXAMPLE 3

2-(4-Fluorophenyl)-3-[2-(S)-(1-phenylethylamino) pyrimidin-4-yl]-5,10-dihydropyrazolo[1,2-b] pthalazin-1-one (8)

Preparation of 1-(4-fluorophenyl)-3-(2-methylsulfanyl-pyrimidin-4-yl)-5,10-dihydropyrazolo[1,2-b]phthalazin-1-one (6): To a solution of 1,2,3,4-tetrahydro-phthalazine, 5, (0.3 g, 1.4 mmol) in pyridine (5 mL) is added 2-(4-fluorophenyl)-3-(2-methylsulfanyl-pyrimidin-4-yl)-3-oxo-propionic acid methyl ester, 3, (0.4 g, 1.4 mmol). The reaction mixture is then heated to reflux for 16 hours. The solvent is removed in vacuo and the resulting residue was purified by preparative HPLC to afford 0.2 g (45% yield) of the desired product as a tan solid.

Preparation of 2-(4-fluorophenyl)-3-(2-methanesulfonyl-pyrimidin-4-yl)-5,10-dihydropyrazolo[1,2-b]phthalazin-1-one (7): To a solution of 1-(4-fluorophenyl)-3-(2-methylsulfanyl-pyrimidin-4-yl)-5,10-dihydropyrazolo[1,2-b]phthalazin-1-one, 6, (2.4 g, 6.8 mmol) in THF:MeOH (80 mL of 1:1 mixture) is added dropwise a solution of OXONE® (16.8 g, 27.2 mmol) in $H_2O$ (80 mL). After stirring for 2 hours at room temperature the reaction mixture is diluted with aqueous saturated $NaHCO_3$ and extracted three times with ethyl acetate. The combined organic phases are dried ($Na_2SO_4$), filtered and concentrated in vacuo to afford 1.5 g (58% yield) of the desired product as a yellow solid.

Preparation of 2-(4-fluorophenyl)-3-[2-(S)-(1-phenylethylamino)pyrimidin-4-yl]-5,10-dihydropyrazolo[1,2-b]phthalazin-1-one (8): 2-(4-fluorophenyl)-3-(2-methanesulfonyl-pyrimidin-4-yl)-5,10-dihydropyrazolo[1,2-b]phthalazin-1-one, 7, (0.9 g, 2.3 mmol) is dissolved in toluene (18 mL) together with (S)-(−)-α-methylbenzylamine (10.5 mL, 81.6 mmol). The resulting mixture is heated to 140° C. for 12 hours, cooled to room temperature and the solvent removed in vacuo. The resulting residue is purified over silica (1:1 EtOAc/hexanes) to afford 0.8 g (80% yield) of the desired product as a red sticky solid.

The first aspect of Category II analogs according to the present invention capable of inhibiting release of inflammatory cytokines relates to compounds comprising a 5,8-dihydro-pyrazolo[1,2-a]-pyridazin-1-one scaffold wherein $R^{2a}$ and $R^{2b}$ are taken together to form a double bond, said scaffold having the formula:

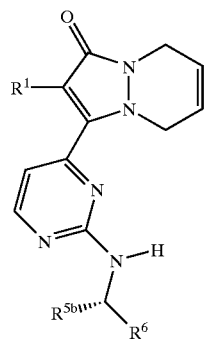

wherein $R^1$, $R^{5b}$, and $R^6$ are described in Table II. The stereochemistry of $R^{5b}$ is the configuration shown when $R^{5b}$ or $R^6$ is not hydrogen.

TABLE II

| No. | $R^1$ | $R^{5b}$ | $R^6$ |
|---|---|---|---|
| 61 | 4-fluorophenyl | H | phenyl |
| 62 | 4-fluorophenyl | H | 4-fluorophenyl |
| 63 | 4-fluorophenyl | H | 2-aminophenyl |
| 64 | 4-fluorophenyl | H | 2-methylphenyl |
| 65 | 4-fluorophenyl | H | 4-methylphenyl |
| 66 | 4-fluorophenyl | H | 4-methoxyphenyl |
| 67 | 4-fluorophenyl | H | 4-(propanesulfonyl)phenyl |
| 68 | 4-fluorophenyl | H | 3-benzo[1,3]dioxol-5-yl |
| 69 | 4-fluorophenyl | H | pyridin-2-yl |
| 70 | 4-fluorophenyl | H | pyridin-3-yl |
| 71 | 4-fluorophenyl | H | H |
| 72 | 4-fluorophenyl | H | methyl |
| 73 | 4-fluorophenyl | H | ethyl |
| 74 | 4-fluorophenyl | H | vinyl |
| 75 | 4-fluorophenyl | H | cyclopropyl |
| 76 | 4-fluorophenyl | H | cyclohexyl |
| 77 | 4-fluorophenyl | H | methoxymethyl |
| 78 | 4-fluorophenyl | H | methoxyethyl |
| 79 | 4-fluorophenyl | H | 1-hydroxy-1-methylethyl |
| 80 | 4-fluorophenyl | H | —$CO_2H$ |
| 81 | 4-fluorophenyl | methyl | phenyl |
| 82 | 4-fluorophenyl | methyl | 4-fluorophenyl |
| 83 | 4-fluorophenyl | methyl | 2-aminophenyl |
| 84 | 4-fluorophenyl | methyl | 2-methylphenyl |
| 85 | 4-fluorophenyl | methyl | 4-methylphenyl |
| 86 | 4-fluorophenyl | methyl | 4-methoxyphenyl |
| 87 | 4-fluorophenyl | methyl | 4-(propanesulfonyl)phenyl |
| 88 | 4-fluorophenyl | methyl | 3-benzo[1,3]dioxol-5-yl |
| 89 | 4-fluorophenyl | methyl | pyridin-2-yl |
| 90 | 4-fluorophenyl | methyl | pyridin-3-yl |
| 91 | 4-fluorophenyl | methyl | H |
| 92 | 4-fluorophenyl | methyl | methyl |
| 93 | 4-fluorophenyl | methyl | ethyl |
| 94 | 4-fluorophenyl | methyl | vinyl |
| 95 | 4-fluorophenyl | methyl | cyclopropyl |
| 96 | 4-fluorophenyl | methyl | cyclohexyl |
| 97 | 4-fluorophenyl | methyl | methoxymethyl |
| 98 | 4-fluorophenyl | methyl | methoxyethyl |
| 99 | 4-fluorophenyl | methyl | 1-hydroxy-1-methylethyl |
| 100 | 4-fluorophenyl | methyl | —$CO_2H$ |

The compounds which comprise the analogs of the first aspect of Category II can be prepared by the synthesis outline herein below in the following scheme.

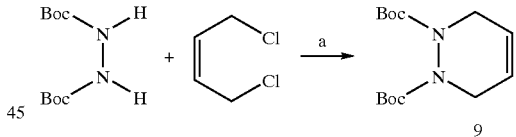

Reagents and conditions: (a) NaH, DMF; 0° C. to 90° C. 4 hr.

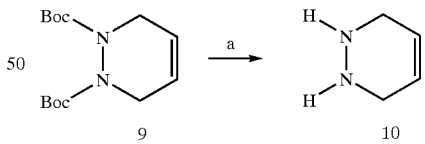

Reagents and conditions: (a) $SOCl_2$, MeOH; 0° C., 17 hr.

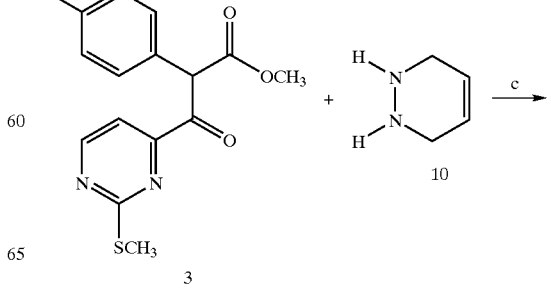

EXAMPLE 4

2-(4-Fluorophenyl)-3-[2-(1-phenylethylamino) pyrimidin-4-yl]-5,8=dihydro-pyrazolo[1,2-a] pyridazin-1-one (13)

Preparation of 3,6-dihydro-pyridazine-1,2-dicarboxylic acid di-tert-butyl ester (9): To a solution of di-tert-butylhydrazodiformate (18.6 g, 80.0 mmol) in DMF (220 mL) cooled to 0° C. is added NaH (8.0 g of a 60% suspension in mineral oil, 200.0 mmol) portionwise. After allowing the solution to warm and stir 45 minutes at room temp, cis-1,4-dichloro-2-butene (8.4 mL, 80.0 mmol) is added dropwise to the reaction mixture. The mixture is then heated at 90° C. for 4 hours, cooled to room temperature and stirred an additional 15 hours. The reaction is quenched by pouring the contents of the reaction vessel into ice water. The resulting aqueous phase is extracted with ether, the combined organic phases washed with aqueous saturated NaHCO₃, dried, filtered and concentrated in vacuo. The obtained crude product is taken up in hexane and the resulting solid recovered by filtration to afford 24 g of the desired product as white powder.

Preparation of 1,2,3,4-tetrahydro-pyridazine (10): To a solution of 3,6-dihydro-pyridazine-1,2-dicarboxylic acid di-tert-butyl ester, 9, (10.0 g, 35.2 mmol) in MeOH (140 mL) at 0° C. is added dropwise $SOCl_2$ (22.0 mL). After gradually warming to room temp and stirring for 17 hours, the solvent is removed in vacuo yielding a tan solid. The isolated solid is then dissolved in MeOH (10 mL) and diluted with ether (250 mL). The resulting white solid is collected by filtration to afford 4.3 g (79% yield) of the desired product as the di-HCl salt.

Preparation of 2-(4-fluorophenyl)-3-(2-methylsulfanyl-pyrimidin-4-yl)-2,3,5,8-tetrahydro-pyrazolo[1,2-a]pyridazin-1-one (11) To a solution of 1,2,3,4-tetrahydro-pyridazine, 5, (5.4 g, 34.2 mmol) in pyridine (100 mL) is added 2-(4-fluorophenyl)-3-(2-methylsulfanyl-pyrimidin-4-yl)-3-oxo-propionic acid methyl ester, 3, (7.3 g, 22.8 mmol). The reaction mixture is heated to 90° C. for 16 hours. The solvent is then removed in vacuo and the resulting residue purified over silica (100% EtOAc) to afford 3.5 g (43% yield) of the desired product as a yellow solid.

Preparation of 2-(4-fluorophenyl)-3-(2-methanesulfonyl-pyrimidin-4-yl)-2,3,5,8-tetrahydro-pyrazolo[1,2-a]pyridazin-1-one (12): To a solution of 2-(4-fluorophenyl)-3-(2-methylsulfanyl-pyrimidin-4-yl)-2,3,5,8-tetrahydro-pyrazolo[1,2-a]pyridazin-1-one, 11, (2.4 g, 6.8 mmol) in THF:MeOH (80 mL of 1:1 mixture) is added dropwise a solution of OXONE® (16.8 g, 27.2 mmol) in $H_2O$ (80 mL). After stirring 2 hours at room temp, the reaction mixture is diluted with aqueous saturated NaHCO₃ and extracted with EtOAc (3×). The combined organic phases are dried, filtered, and concentrated in vacuo to afford 1.5 g (58% yield) of the desired product as a yellow solid.

Preparation of 2-(4-fluorophenyl)-3-[2-(1-(S)-phenylethylamino)pyrimidin-4-yl]-5,8-dihydropyrazolo[1,2-a]pyridazin-1-one (13): 2-(4-Fluorophenyl)-3-(2-methanesulfonyl-pyrimidin-4-yl)-2,3,5,8-tetrahydro-pyrazolo[1,2-a]pyridazin-1-one, 12, (0.9 g, 2.3 mmol) is dissolved in toluene (18 mL) and (S)-(−)-α-methylbenzylamine (10.5 mL, 81.6 mmol) added. The

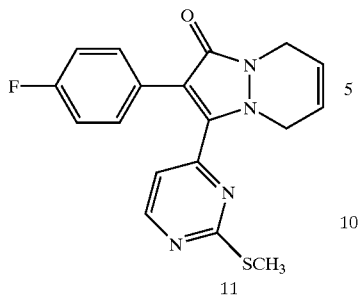

Reagents and conditions: (c) pyridine, 90° C., 16 hr.

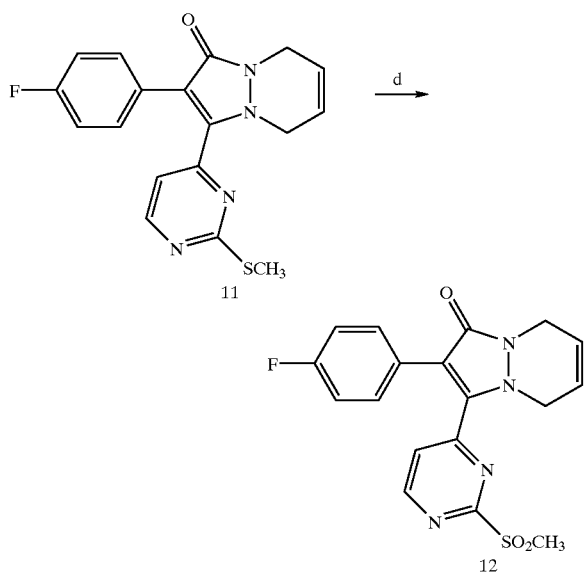

Reagents and conditions: (d) OXONE®, THF/MeOH/water; rt 2 hr.

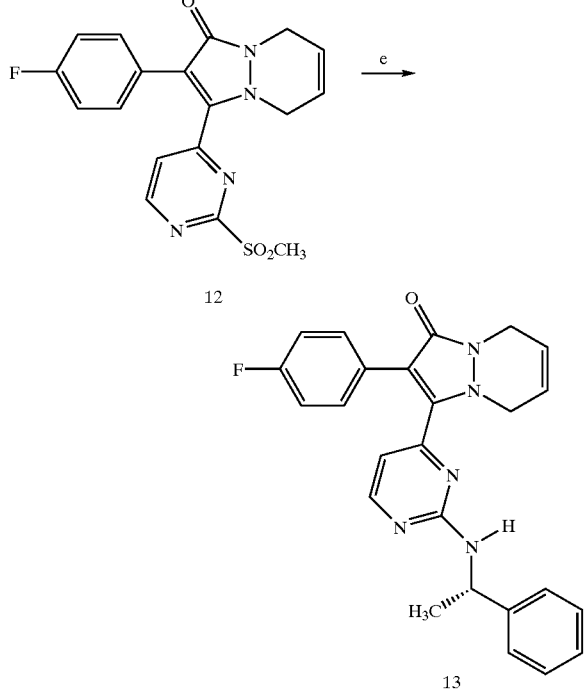

Reagents and conditions: (e) (S)-(−)-α-methylenzylamine, toluene; 140° C. for 12 hr.

resulting mixture is heated to 140° C. for 12 hours, cooled, and the solvent removed in vacuo. The resulting crude product is purified over silica (1:1 EtOAc/hexanes) to afford 0.8 g (80% yield) of the desired product as a red sticky solid.

The second aspect of Category II analogs according to the present invention capable of inhibiting release of inflammatory cytokines relates to compounds comprising a 5,6,7,8-tetrahydro-pyrazolo[1,2-a]-pyridazin-1-one scaffold having the formula:

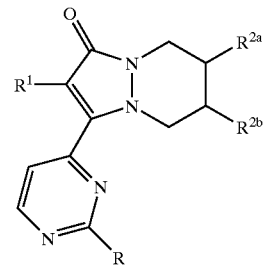

wherein R, $R^1$, $R^{2a}$, and $R^{2b}$ are described herein Table III

TABLE III

| No. | $R^1$ | $R^{2a}$ | $R^{2b}$ | R |
|---|---|---|---|---|
| 101 | 4-fluorophenyl | H | —OH | 1-(S)-phenylethylamino |
| 102 | 4-fluorophenyl | H | —OH | 1-(S)-(4-fluorophenyl)ethylamino |
| 103 | 4-fluorophenyl | H | —OH | 1-(S)-(2-aminophenyl)ethylamino |
| 104 | 4-fluorophenyl | H | —OH | 1-(S)-(2-methylphenyl)ethylamino |
| 105 | 4-fluorophenyl | H | —OH | 1-(S)-(4-methylphenyl)ethylamino |
| 106 | 4-fluorophenyl | H | —OH | 1-(S)-(4-methoxyphenyl)ethylamino |
| 107 | 4-fluorophenyl | H | —OH | 1-(S)-(4-propanesulfonylphenyl)ethylamino |
| 108 | 4-fluorophenyl | H | —OH | 1-(S)-(3-benzo[1,3]dioxol-5-yl)ethylamino |
| 109 | 4-fluorophenyl | H | —OH | 1-(S)-(pyridin-2-yl)ethylamino |
| 110 | 4-fluorophenyl | H | —OH | 1-(S)-(pyridin-3-yl)ethylamino |
| 111 | 4-fluorophenyl | H | —OH | methylamino |
| 112 | 4-fluorophenyl | H | —OH | ethylamino |
| 113 | 4-fluorophenyl | H | —OH | propylamino |
| 114 | 4-fluorophenyl | H | —OH | cyclopropylamino |
| 115 | 4-fluorophenyl | H | —OH | cyclopropylmethylamino |
| 116 | 4-fluorophenyl | H | —OH | tert-butylamino |
| 117 | 4-fluorophenyl | H | —OH | 1-(S)-(cyclopropyl)ethylamino |
| 118 | 4-fluorophenyl | H | —OH | 1-(S)-(cyclopropylmethyl)ethylamino |
| 119 | 4-fluorophenyl | H | —OH | 1-(R)-(α)-(carboxy)benzylamino |
| 120 | 4-fluorophenyl | H | —OH | 1-(S)-(α)-(methyl)benzylamino |
| 121 | 4-fluorophenyl | —OH | —OH | 1-(S)-phenylethylamino |
| 122 | 4-fluorophenyl | —OH | —OH | 1-(S)-(4-fluorophenyl)ethylamino |
| 123 | 4-fluorophenyl | —OH | —OH | 1-(S)-(2-aminophenyl)ethylamino |
| 124 | 4-fluorophenyl | —OH | —OH | 1-(S)-(2-methylphenyl)ethylamino |
| 125 | 4-fluorophenyl | —OH | —OH | 1-(S)-(4-methylphenyl)ethylamino |
| 126 | 4-fluorophenyl | —OH | —OH | 1-(S)-(4-methoxyphenyl)ethylamino |
| 127 | 4-fluorophenyl | —OH | —OH | 1-(S)-(4-propanesulfonylphenyl)ethylamino |
| 128 | 4-fluorophenyl | —OH | —OH | 1-(S)-(3-benzo[1,3]dioxol-5-yl)ethylamino |
| 129 | 4-fluorophenyl | —OH | —OH | 1-(S)-(pyridin-2-yl)ethylamino |
| 130 | 4-fluorophenyl | —OH | —OH | 1-(S)-(pyridin-3-yl)ethylamino |
| 131 | 4-fluorophenyl | —OH | —OH | methylamino |
| 132 | 4-fluorophenyl | —OH | —OH | ethylamino |
| 133 | 4-fluorophenyl | —OH | —OH | propylamino |
| 134 | 4-fluorophenyl | —OH | —OH | cyclopropylamino |
| 135 | 4-fluorophenyl | —OH | —OH | cyclopropylmethylamino |
| 136 | 4-fluorophenyl | —OH | —OH | tert-butylamino |
| 137 | 4-fluorophenyl | —OH | —OH | 1-(S)-(cyclopropyl)ethylamino |
| 138 | 4-fluorophenyl | —OH | —OH | 1-(S)-(cyclopropylmethyl)ethylamino |
| 139 | 4-fluorophenyl | —OH | —OH | 1-(R)-(α)-(carboxy)benzylamino |
| 140 | 4-fluorophenyl | —OH | —OH | 1-(S)-(α)-(methyl)benzylamino |
| 141 | 4-fluorophenyl | —OCH₃ | —OCH₃ | 1-(S)-phenylethylamino |
| 142 | 4-fluorophenyl | —OCH₃ | —OCH₃ | 1-(S)-(4-fluorophenyl)ethylamino |
| 143 | 4-fluorophenyl | —OCH₃ | —OCH₃ | 1-(S)-(2-aminophenyl)ethylamino |
| 144 | 4-fluorophenyl | —OCH₃ | —OCH₃ | 1-(S)-(2-methylphenyl)ethylamino |
| 145 | 4-fluorophenyl | —OCH₃ | —OCH₃ | 1-(S)-(4-methylphenyl)ethylamino |
| 146 | 4-fluorophenyl | —OCH₃ | —OCH₃ | 1-(S)-(4-methoxyphenyl)ethylamino |
| 147 | 4-fluorophenyl | —OCH₃ | —OCH₃ | 1-(S)-(4-propanesulfonylphenyl)ethylamino |
| 148 | 4-fluorophenyl | —OCH₃ | —OCH₃ | 1-(S)-(3-benzo[1,3]dioxol-5-yl)ethylamino |
| 149 | 4-fluorophenyl | —OCH₃ | —OCH₃ | 1-(S)-(pyridin-2-yl)ethylamino |
| 150 | 4-fluorophenyl | —OCH₃ | —OCH₃ | 1-(S)-(pyridin-3-yl)ethylamino |
| 151 | 4-fluorophenyl | —OCH₃ | —OCH₃ | methylamino |
| 152 | 4-fluorophenyl | —OCH₃ | —OCH₃ | ethylamino |
| 153 | 4-fluorophenyl | —OCH₃ | —OCH₃ | propylamino |
| 154 | 4-fluorophenyl | —OCH₃ | —OCH₃ | cyclopropylamino |
| 155 | 4-fluorophenyl | —OCH₃ | —OCH₃ | cyclopropylmethylamino |
| 156 | 4-fluorophenyl | —OCH₃ | —OCH₃ | tert-butylamino |
| 157 | 4-fluorophenyl | —OCH₃ | —OCH₃ | 1-(S)-(cyclopropyl)ethylamino |
| 158 | 4-fluorophenyl | —OCH₃ | —OCH₃ | 1-(S)-(cyclopropylmethyl)ethylamino |
| 159 | 4-fluorophenyl | —OCH₃ | —OCH₃ | 1-(R)-(α)-(carboxy)benzylamino |
| 160 | 4-fluorophenyl | —OCH₃ | —OCH₃ | 1-(S)-(α)-(methyl)benzylamino |

For the second aspect of Category II, intermediates such as compound 13, can be utilized to prepare the analogs listed in Table IV, for example, compound 14.

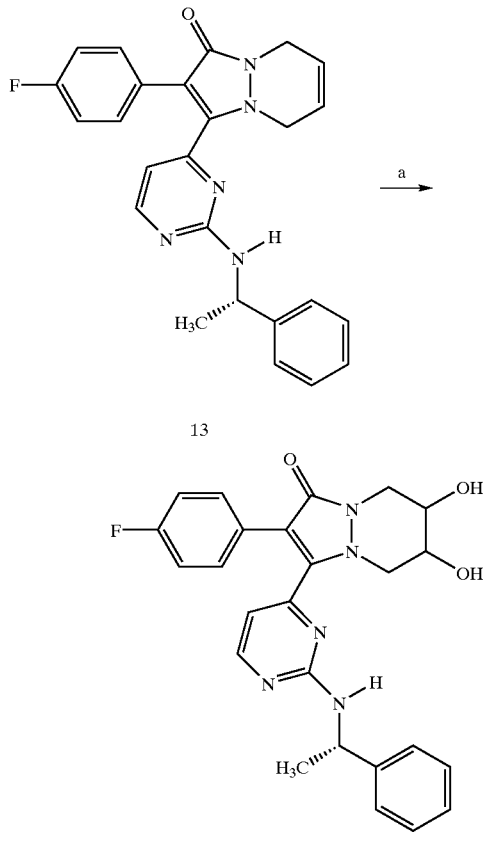

13

14
Reagents and conditions: (a) OsO₄, K₃Fe(CN)₆; t-BuOH:H₂O, rt 12 hr.

EXAMPLE 5

2-(4-Fluorophenyl)-6,7-dihydroxy-3-[2-(1-phenylethylamino)pyrimidin-4-yl]-5,6,7,8=tetrahydropyrazolo[1,2-a]pyridazin-1-one (14)

Preparation of 2-(4-Fluorophenyl)-6,7-dihydroxy-3-[2-(1-phenylethylamino)-pyrimidin-4-yl]-5,6,7,8-tetrahydropyrazolo[1,2-a]pyridazin-1-one (14): To a solution of 2-(4-fluorophenyl)-3-[2-(1-phenylethylamino)pyrimidin-4-yl]-5,8-dihydro-pyrazolo[1,2-a]pyridazin-1-one, 13, (0.8 g, 1.88 mmol) in t-BuOH:H₂O (24 mL of 1:1 mixture) is added K₃Fe(CN)₆ (1.9 g, 5.64 mmol), K₂CO₃ (0.8 g, 5.6 mmol) and NaHCO₃ (0.5 g, 5.6 mmol), followed by osmium tetroxide (0.1 g, 0.3 mmol). The resulting mixture is stirred at room temperature for 12 hours. The reaction is quenched by the addition of aqueous saturated KHSO₄ solution (10 mL). The aqueous phase is extracted with EtOAc (3×) and the combined organic phases are dried, filtered and concentrated in vacuo. The resulting crude product is purified over silica (100% EtOAc) to afford 0.4 g (48% yield) of the desired product.

In addition, a compound such as 14 can itself be utilized as an intermediate to other analogs, for example, compound 15.

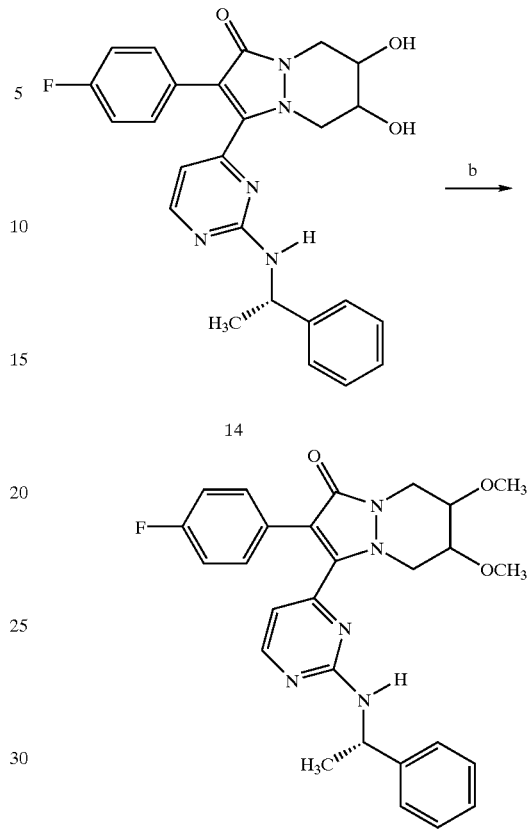

14

15

Reagents and conditions: (b) NaH, CH₃I, toluene, rt 62 hr.

EXAMPLE 6

2-(4-Fluorophenyl)-6,7-dimethoxy-3-[2-(1-(S)-phenylethylamino)pyrimidin-4-yl]-5,6,7,8-tetrahydropyrazolo[1,2-a]pyridazin-1-one (15)

Preparation of 2-(4-fluorophenyl)-6,7-dimethoxy-3-[2-(1-(S)-phenylethylamino)-pyrimidin-4-yl]-5,6,7,8-tetrahydropyrazolo[1,2-a]pyridazin-1-one (15): To a solution of 2-(4-fluorophenyl)-6,7-dihydroxy-3-[2-(1-phenylethylamino)pyrimidin-4-yl]-5,6,7,8-tetrahydropyrazolo-[1,2-a]pyridazin-1-one, 14, (0.42 g, 0.91 mmol) in THF (2 mL) is added NaH (0.09 g, 2.30 mmol). After stirring at room temp for 1 hour, methyl iodide (0.14 g, 2.30 mmol) is added dropwise to the reaction mixture. After stirring for 62 hours at room temp, the mixture is concentrated in vacuo, dissolved in EtOAc and washed with aqueous saturated NaHCO₃. The organic phase is dried, filtered, concentrated in vacuo and the resulting residue purified over silica (100% EtOAc) to afford 0.07 g (16% yield) of the desired product as a yellow solid.

The first aspect of Category III analogs according to the present invention capable of inhibiting release of inflammatory cytokines relates to compounds comprising a 5,6,7,8-tetrahydro-pyrazolo[1,2-a]-pyridazin-1-one scaffold having the formula:

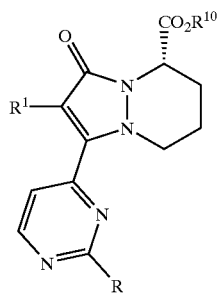

wherein R comprises an ether R, $R^1$ and $R^{10}$ are described herein below in Table II and the analogs have the indicated stereochemistry.

TABLE IV

| No. | $R^{10}$ | $R^1$ | R |
|---|---|---|---|
| 61 | H | 4-fluorophenyl | phenoxy |
| 62 | H | 4-fluorophenyl | 2-fluorophenoxy |
| 63 | H | 4-fluorophenyl | 3-fluorophenoxy |
| 64 | H | 4-fluorophenyl | 4-fluorophenoxy |
| 65 | H | 4-fluorophenyl | 2,6-difluorophenoxy |
| 66 | H | 4-fluorophenyl | 2-cyanophenoxy |
| 67 | H | 4-fluorophenyl | 3-cyanophenoxy |
| 68 | H | 4-fluorophenyl | 2-trifluoromethylphenoxy |
| 69 | H | 4-fluorophenyl | 4-trifluoromethylphenoxy |
| 70 | H | 4-fluorophenyl | 2-methylphenoxy |
| 71 | H | 4-fluorophenyl | 4-methylphenoxy |
| 72 | H | 4-fluorophenyl | 2,4-dimethylphenoxy |
| 73 | H | 4-fluorophenyl | 3-N-acetylaminophenoxy |
| 74 | H | 4-fluorophenyl | 2-methoxyphenoxy |
| 75 | H | 4-fluorophenyl | 4-methoxyphenoxy |
| 76 | H | 4-fluorophenyl | 3-benzo[1,3]dioxol-5-yl |
| 77 | methyl | 4-fluorophenyl | phenoxy |
| 78 | methyl | 4-fluorophenyl | 2-fluorophenoxy |
| 79 | methyl | 4-fluorophenyl | 3-fluorophenoxy |
| 80 | methyl | 4-fluorophenyl | 4-fluorophenoxy |
| 81 | methyl | 4-fluorophenyl | 2,6-difluorophenoxy |
| 82 | methyl | 4-fluorophenyl | 2-cyanophenoxy |
| 83 | methyl | 4-fluorophenyl | 3-cyanophenoxy |
| 84 | methyl | 4-fluorophenyl | 2-trifluoromethylphenoxy |
| 85 | methyl | 4-fluorophenyl | 4-trifluoromethylphenoxy |
| 86 | methyl | 4-fluorophenyl | 2-methylphenoxy |
| 87 | methyl | 4-fluorophenyl | 4-methylphenoxy |
| 88 | methyl | 4-fluorophenyl | 2,4-dimethylphenoxy |
| 89 | methyl | 4-fluorophenyl | 3-N-acetylaminophenoxy |
| 90 | methyl | 4-fluorophenyl | 2-methoxyphenoxy |
| 91 | methyl | 4-fluorophenyl | 4-methoxyphenoxy |
| 92 | methyl | 4-fluorophenyl | 3-benzo[1,3]dioxol-5-yl |
| 93 | H | 4-chlorophenyl | phenoxy |
| 94 | H | 4-chlorophenyl | 2-fluorophenoxy |
| 95 | H | 4-chlorophenyl | 3-fluorophenoxy |
| 96 | H | 4-chlorophenyl | 4-fluorophenoxy |
| 97 | H | 4-chlorophenyl | 2,6-difluorophenoxy |
| 98 | H | 4-chlorophenyl | 2-cyanophenoxy |
| 99 | H | 4-chlorophenyl | 3-cyanophenoxy |
| 100 | H | 4-chlorophenyl | 2-trifluoromethylphenoxy |
| 101 | H | 4-chlorophenyl | 4-trifluoromethylphenoxy |
| 102 | H | 4-chlorophenyl | 2-methylphenoxy |
| 103 | H | 4-chlorophenyl | 4-methylphenoxy |
| 104 | H | 4-chlorophenyl | 2,4-dimethylphenoxy |
| 105 | H | 4-chlorophenyl | 3-N-acetylaminophenoxy |
| 106 | H | 4-chlorophenyl | 2-methoxyphenoxy |
| 107 | H | 4-chlorophenyl | 4-methoxyphenoxy |
| 108 | H | 4-chlorophenyl | 3-benzo[1,3]dioxol-5-yl |
| 109 | methyl | 4-chlorophenyl | phenoxy |
| 110 | methyl | 4-chlorophenyl | 2-fluorophenoxy |
| 111 | methyl | 4-chlorophenyl | 3-fluorophenoxy |
| 112 | methyl | 4-chlorophenyl | 4-fluorophenoxy |
| 113 | methyl | 4-chlorophenyl | 2,6-difluorophenoxy |
| 114 | methyl | 4-chlorophenyl | 2-cyanophenoxy |
| 115 | methyl | 4-chlorophenyl | 3-cyanophenoxy |
| 116 | methyl | 4-chlorophenyl | 2-trifluoromethylphenoxy |
| 117 | methyl | 4-chlorophenyl | 4-trifluoromethylphenoxy |
| 118 | methyl | 4-chlorophenyl | 2-methylphenoxy |
| 119 | methyl | 4-chlorophenyl | 4-methylphenoxy |
| 120 | methyl | 4-chlorophenyl | 2,4-dimethylphenoxy |
| 121 | methyl | 4-chlorophenyl | 3-N-acetylaminophenoxy |
| 122 | methyl | 4-chlorophenyl | 2-methoxyphenoxy |
| 123 | methyl | 4-chlorophenyl | 4-methoxyphenoxy |
| 124 | methyl | 4-chlorophenyl | 3-benzo[1,3]dioxol-5-yl |

The compounds which comprise the analogs of the first aspect of Category III can be prepared by the synthesis outline herein below in the following scheme.

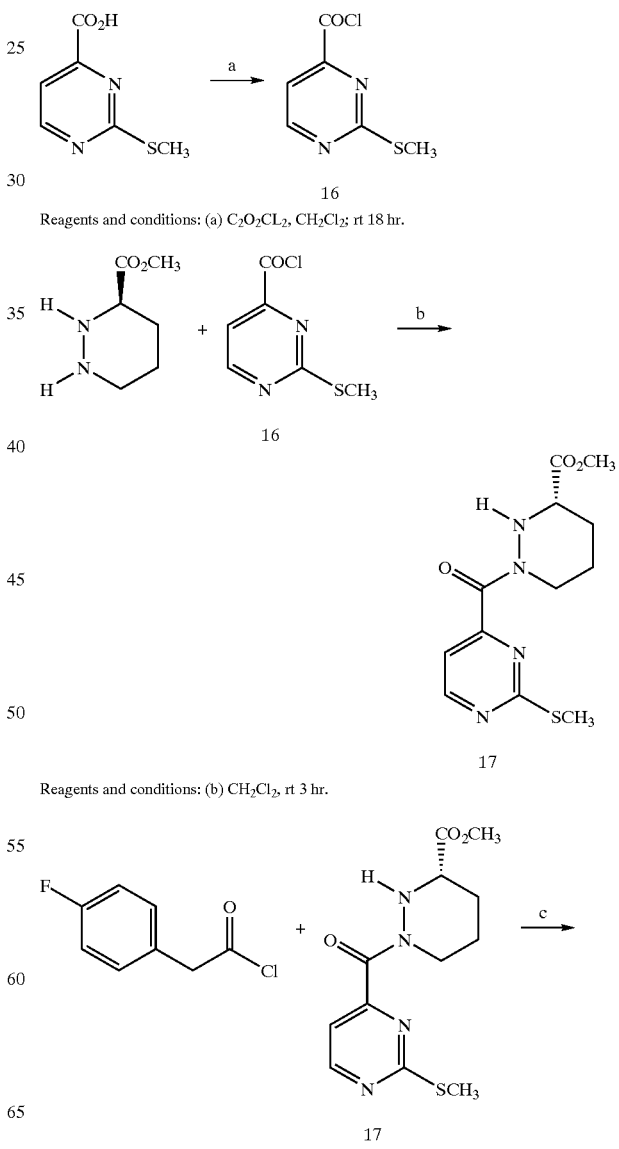

Reagents and conditions: (a) $C_2O_2Cl_2$, $CH_2Cl_2$; rt 18 hr.

Reagents and conditions: (b) $CH_2Cl_2$, rt 3 hr.

29

-continued

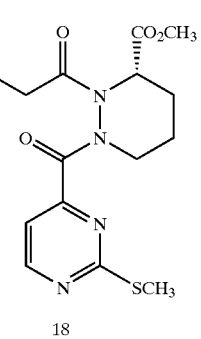

18

Reagents and conditions: (c) TEA, CH₂Cl₂,; rt 18 hr.

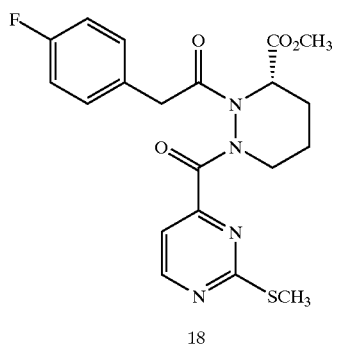

18

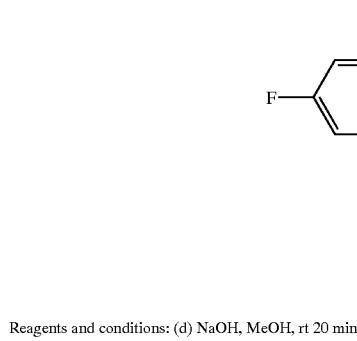

19

Reagents and conditions: (d) NaOH, MeOH, rt 20 min.

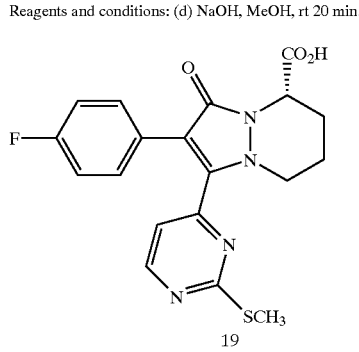

19

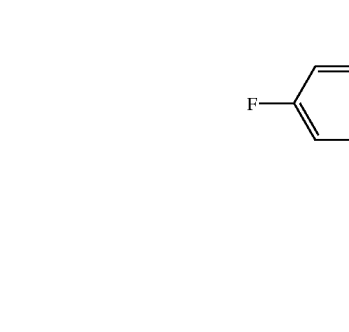

20

30

-continued

Reagents and conditions: (e) TMS—CHN₂, CH₂Cl₂/MeOH; 20 min rt.

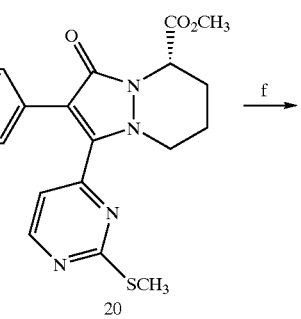

20

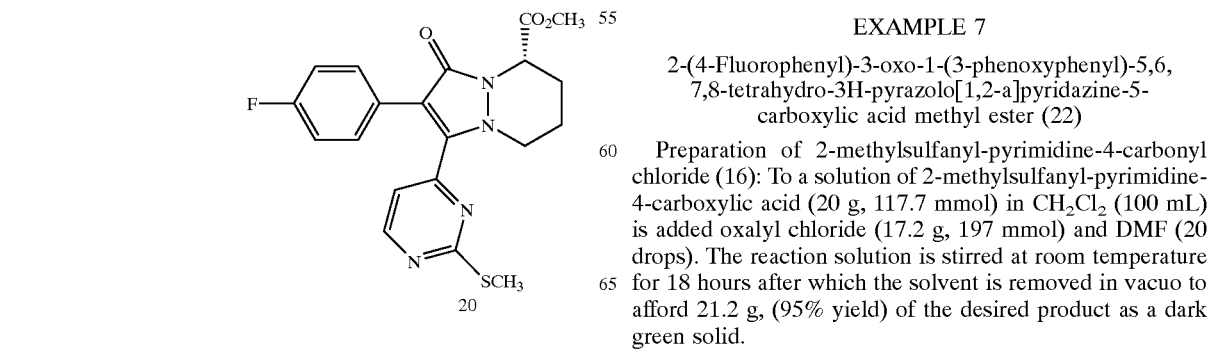

21

Reagents and conditions: (f) OXONE®, THF/MeOH, rt 4 hr.

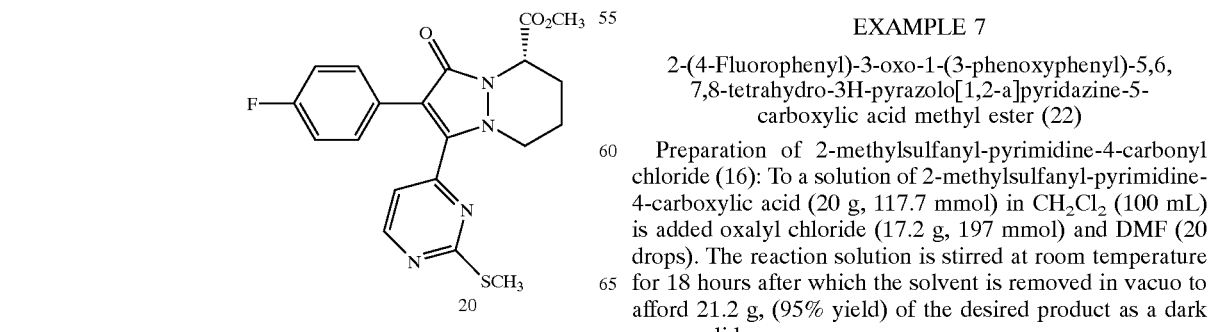

21

22

Reagents and conditions: (g) phenol, NaH, THF; rt 1 hr.

EXAMPLE 7

2-(4-Fluorophenyl)-3-oxo-1-(3-phenoxyphenyl)-5,6,7,8-tetrahydro-3H-pyrazolo[1,2-a]pyridazine-5-carboxylic acid methyl ester (22)

Preparation of 2-methylsulfanyl-pyrimidine-4-carbonyl chloride (16): To a solution of 2-methylsulfanyl-pyrimidine-4-carboxylic acid (20 g, 117.7 mmol) in CH₂Cl₂ (100 mL) is added oxalyl chloride (17.2 g, 197 mmol) and DMF (20 drops). The reaction solution is stirred at room temperature for 18 hours after which the solvent is removed in vacuo to afford 21.2 g, (95% yield) of the desired product as a dark green solid.

Preparation of 1-(methylsulfanyl-pyrimidine-4-carbonyl) hexahydro-pyridazine-3-carboxylic acid methyl ester (17): To a solution of hexahydro-pyridazine-3-carboxylic acid methyl ester (1.5 g, 8.3 mmol) in CH$_2$Cl$_2$ (80 mL) is added 2-methylsulfanyl-pyrimidine-4-carbonyl chloride, 16, (1.41 g, 7.5 mmol) and triethylamine (1.2 mL, 8.3 mmol). The mixture is stirred at room temperature for 3 hours. The reaction solution is then diluted with1 N HCl (100 mL) and the organic phase is decanted. The aqueous phase is extracted with additional solvent and the organic layers are combined, dried, and concentrated in vacuo. The crude product is purified over silica(ethyl acetate/hexane 1:1) to afford 0.9 g (36% yield) of the desired product as a yellow solid.

Preparation of 2-(4-fluorobenzoyl)-1-(2-methylsulfanyl-pyrimidine-4-carbonyl)-hexahydro-pyridazine-3-carboxylic acid methyl ester (18): To a solution of 1-(methylsulfanyl-pyrimidine-4-carbonyl)hexahydro-pyridazine-3-carboxylic acid methyl ester, 17, (0.9 g, 3 mmol) in CH$_2$Cl$_2$ (80 mL) is added 4-fluorophenylacetyl chloride (0.63 mL, 4.6 mmol) and triethylamine (0.55 mL, 3.6 mmol). The reaction solution is stirred at room temperature for 18 hours then dilute with 1 N HCl (50 mL) and the organic layer decanted. The organic phase is extracted with additional solvent, the organic layers are combined, dried, and concentrated in vacuo to afford the crude product. The crude material is purified over silica (ethyl acetate/hexane 1:1) to afford 1.15 g (89% yield) of the desired product as a yellow solid.

Preparation of 2-(4-fluorophenyl)-1-(3-methylsulfanyl-pyrimidin-4-yl)-3-oxo-5,6,7,8-tetrahydro-3H-pyrazolo[1,2-a]pyridazine-5-carboxylic acid (19): To a solution of 2-(4-fluorobenzoyl)-1-(2-methylsulfanyl-pyrimidine-4-carbonyl)-hexahydro-pyridazine-3-carboxylic acid methyl ester, 18, (1.13 g, 2.62 mmol) in methanol (40 mL) is added NaOH (1.26 g, 31.4 mmol). The reaction is stirred at room temperature for 20 minutes then diluted wit 1 N HCl (50 mL). The solution is extracted with ethyl acetate (3×250 mL), the organic layers are combined, dried, and concentrated in vacuo to afford 0.83 g (79% yield) of an oil which is used without further purification.

Preparation of 2-(4-fluorophenyl)-1-(3-methylsulfanyl-pyrimidin-4-yl)-3-oxo-5,6,7,8-tetrahydro-3H-pyrazolo[1,2-a]pyridazine-5-carboxylic acid methyl ester (20): To a solution of 2-(4fluorophenyl)-1-(3-methylsulfanylphenyl)-3-oxo-5,6,7,8-tetrahydro-3H-pyrazolo[1,2-a]pyridazine-5-carboxylic acid, 19, (0.83 g, 2.1 mmol) in methylene chloride (50 mL) is added trimethylsilyl-diazomethane (1.5 mL of a 2 M solution is hexane, 3 mmol). The reaction is stirred for 20 minutes at room temperature then concentrated in vacuo to afford the crude product as an oil which is purified over silica (hexane/ethyl acetate 1:4) to afford 0.51 g (59% yield) of the desired product as a yellow foam.

Preparation of 2-(4fluorophenyl)-1-(3-methanesulfonyl-pyrimidin-4-yl)-3-oxo-5,6,7,8-tetrahydro-3H-pyrazolo[1,2-a]pyridazine-5-carboxylic acid methyl ester (21): To a stirred solution of Preparation of 2-(4fluorophenyl)-1-(3-methylsulfanylphenyl)-3-oxo-5,6,7,8-tetrahydro-3H-pyrazolo[1,2-a]pyridazine-5-carboxylic acid methyl ester, 20, (0.51, 1.23 mmol) in methanol (30 mL) is cooled to 0° C. Oxone® (2.27 g, 3.7 mmol) is dissolved in water (30 mL) and added dropwise to the reaction solution over 1 hour. The solution is allowed to warm to room temperature and stir a total of 3 additional hours. NaHCO$_3$ (sat.) is added until the pH is about 7. The reaction solution is then extracted several times with ethyl acetate, the organic phases combined, dried, and concentrated in vacuo to afford 0.5 g (91% yield) of the desired product as a yellow foam.

Preparation of 2-(4-fluorophenyl)-1-(2-phenoxy-pyrimidin-4-yl)-3-oxo-5,6,7,8-tetrahydro-3H-pyrazolo[1,2-a]pyridazine-5-carboxylic acid methyl ester (22): To a solution of 2-(4fluorophenyl)-1-(3-methanesulfonyl-pyrimidin-4-yl)-3-oxo-5,6,7,8-tetrahydro-3H-pyrazolo[1,2-a] pyridazine-5-carboxylic acid methyl ester, 21, (0.033 g, 0.074 mmol) in THF (3 mL) is added phenol and NaH (0.009 g, 0.22 mmol). The reaction mixture is stirred at room temperature for 1 hour. The reaction is quenched by the addition of 1 N HCl (20 mL) and the solution is extracted with ethyl acetate (3×25 mL). The organic phases are combined, washed with brine, dried, and concentrated in vacuo to afford the crude product which is purified over silica (hexanes/ethyl acetate 1:3) to afford 0.012 g (35% yield) of the desired product as a white solid. $^1$H NMR (300 MHz, CDCl$_3$) δ 8.64 (d, J=4.6 Hz 1 H), 7.59–7.63 (m, 2 H), 7.40–7.45 (m, 3 H), 7.28–7.30 (m, 1 H), 7.18 (d, J=8.4 Hz, 2 H), 7.03–7.08 (m, 2 H), 4.50–4.56 (m, 1 H), 3.99–4.04 (m, 1 H), 3.86 (s, 1 H), 3.01–3.10 (m, 1 H), 2.33–2.41 (m, 1 H), 1.86 (brs, 2 H), 1.64 (brs, 3 H); ESI/MS: 461 (M+H).

Other compounds according to this aspect of Category III can be formed by the following procedure.

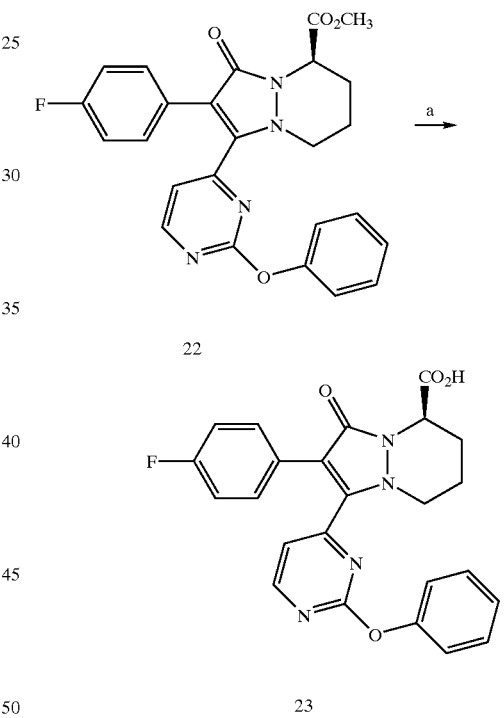

Reagents and conditions: (a) LiOh, MeOH/water, ret, 3 hr.

EXAMPLE 8

Preparation of 2-(4-fluorophenyl)-1-(2-phenoxy-pyrimidin-4-yl)-3-oxo-5,6,7,8-tetrahydro-3H-pyrazolo[1,2-a]pyridazine-5-carboxylic acid (23): To a solution of 2-(4-fluorophenyl)-1-(2-phenoxy-pyrimidin-4-yl)-3-oxo-5,6,7,8-tetrahydro-3H-pyrazolo[1,2-a]pyridazine-5-carboxylic acid methyl ester, 22, (0.02 g, 0.0143 mmol) in methanol (1 mL) and water (1 mL) is added LiOH (0.016 g, 0.65 mmol). The reaction solution is stirred at room temperature for 3 hours then quenched by the addition of 1 N HCl (20 mL). The reaction solution is extracted with ethyl acetate (3×50 mL), the organic layers are combined, washed with brine, dried, and concentrated in vacuo to afford 0.012 g (63% yield) of the desired product as a yellow solid. $^1$H NMR (300 MHz, CDCl$_3$) δ 8.45 (dd, J=4.6, 2.1 Hz, 1 H), 7.14–7.44 (m, 7 H), 6.84–6.95 (m, 3 H), 4.93 (dd, J=11.7, 9.3 Hz, 1 H), 4.23 (br d, J=12.9 Hz, 1 H), 3.04–3.11 (m, 1H), 2.46–2.52 (m, 2 H), 1.71–1.93 (m, 2 H), APCI/MS: 447 (M+H).

2-(4-Fluorophenyl)-1-[2-(4-fluorophenoxy)pyrimidin-4-yl]-3-oxo-5,6,7,8-tetrahydro-3H-pyrazolo[1,2-a]pyridazine-5-carboxylic acid: $^1$H NMR (300 MHz, CDCl$_3$) δ 8.50 (d, J=5.1 Hz, 1 H), 7.36 (dd, J=8.7, 5.4 Hz, 2 H), 7.20–7.31 (m, 4 H), 7.02 (t, J=8.7 Hz, 2 H), 6.97 (d, J=5.1 Hz, 1 H), 5.23–5.25 (m, 1 H), 4.24 (d, J=11.4 Hz, 1 H), 3.74 (s, 3H), 2.94–2.99 (m, 1 H), 2.54–2.59 (m, 1 H), 1.82–2.00 (m, 3 H); ESI/MS: 479 (M+H).

The second aspect of Category III analogs according to the present invention capable of inihibiting release of inflammatory cytokines relates to compounds comprising a 5,6,7,8-tetrahydro-pyrazolo[1,2-a]-pyridazin-1-one scaffold having the formula:

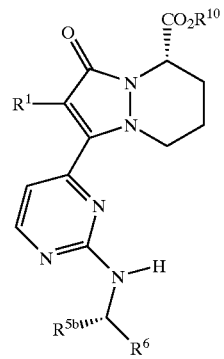

wherein R units are amines having the formula —NH[CHR$^{5b}$]R$^6$, and R$^1$, R$^{5b}$, R$^6$, and R$^{10}$ are described herein below in Table I. The stereochemistry of R$^{5b}$ is the configuration shown when R$^{5b}$ is not hydrogen.

TABLE V

| No. | R$^1$ | R$^{5b}$ | R$^6$ | R$^{10}$ |
|---|---|---|---|---|
| 125 | 4-fluorophenyl | H | H | H |
| 126 | 4-fluorophenyl | H | methyl | H |
| 127 | 4-fluorophenyl | H | ethyl | H |
| 128 | 4-fluorophenyl | H | vinyl | H |
| 129 | 4-fluorophenyl | H | cyclopropyl | H |
| 130 | 4-fluorophenyl | H | cyclohexyl | H |
| 131 | 4-fluorophenyl | H | methoxymethyl | H |
| 132 | 4-fluorophenyl | H | methoxyethyl | H |
| 133 | 4-fluorophenyl | H | 1-hydroxy-1-methylethyl | H |
| 134 | 4-fluorophenyl | H | —CO$_2$H | H |
| 135 | 4-fluorophenyl | H | phenyl | H |
| 136 | 4-fluorophenyl | H | 4-fluorophenyl | H |
| 137 | 4-fluorophenyl | H | 2-aminophenyl | H |
| 138 | 4-fluorophenyl | H | 2-methylphenyl | H |
| 139 | 4-fluorophenyl | H | 4-methylphenyl | H |
| 140 | 4-fluorophenyl | H | 4-methoxyphenyl | H |
| 141 | 4-fluorophenyl | H | 4-(propanesulfonyl)phenyl | H |
| 142 | 4-fluorophenyl | H | 3-benzo[1,3]dioxol-5-yl | H |
| 143 | 4-fluorophenyl | H | pyridin-2-yl | H |
| 144 | 4-fluorophenyl | H | pyridin-3-yl | H |
| 145 | 4-fluorophenyl | methyl | H | H |
| 146 | 4-fluorophenyl | methyl | methyl | H |
| 147 | 4-fluorophenyl | methyl | ethyl | H |
| 148 | 4-fluorophenyl | methyl | vinyl | H |
| 149 | 4-fluorophenyl | methyl | cyclopropyl | H |
| 150 | 4-fluorophenyl | methyl | cyclohexyl | H |
| 151 | 4-fluorophenyl | methyl | methoxymethyl | H |
| 152 | 4-fluorophenyl | methyl | methoxyethyl | H |
| 153 | 4-fluorophenyl | methyl | 1-hydroxy-1-methylethyl | H |
| 154 | 4-fluorophenyl | methyl | —CO$_2$H | H |
| 155 | 4-fluorophenyl | methyl | phenyl | H |
| 156 | 4-fluorophenyl | methyl | 4-fluorophenyl | H |
| 157 | 4-fluorophenyl | methyl | 2-aminophenyl | H |
| 158 | 4-fluorophenyl | methyl | 2-methylphenyl | H |
| 159 | 4-fluorophenyl | methyl | 4-methylphenyl | H |
| 160 | 4-fluorophenyl | methyl | 4-methoxyphenyl | H |
| 161 | 4-fluorophenyl | methyl | 4-(propanesulfonyl)phenyl | H |
| 162 | 4-fluorophenyl | methyl | 3-benzo[1,3]dioxol-5-yl | H |
| 163 | 4-fluorophenyl | methyl | pyridin-2-yl | H |
| 164 | 4-fluorophenyl | methyl | pyridin-3-yl | H |
| 165 | 4-fluorophenyl | H | H | methyl |
| 166 | 4-fluorophenyl | H | methyl | methyl |
| 167 | 4-fluorophenyl | H | ethyl | methyl |
| 168 | 4-fluorophenyl | H | vinyl | methyl |
| 169 | 4-fluorophenyl | H | cyclopropyl | methyl |
| 170 | 4-fluorophenyl | H | cyclohexyl | methyl |
| 171 | 4-fluorophenyl | H | methoxymethyl | methyl |
| 172 | 4-fluorophenyl | H | methoxyethyl | methyl |
| 173 | 4-fluorophenyl | H | 1-hydroxy-1-methylethyl | methyl |
| 174 | 4-fluorophenyl | H | —CO$_2$H | methyl |
| 175 | 4-fluorophenyl | H | phenyl | methyl |
| 176 | 4-fluorophenyl | H | 4-fluorophenyl | methyl |
| 177 | 4-fluorophenyl | H | 2-aminophenyl | methyl |
| 178 | 4-fluorophenyl | H | 2-methylphenyl | methyl |
| 179 | 4-fluorophenyl | H | 4-methylphenyl | methyl |
| 180 | 4-fluorophenyl | H | 4-methoxyphenyl | methyl |
| 181 | 4-fluorophenyl | H | 4-(propanesulfonyl)phenyl | methyl |
| 182 | 4-fluorophenyl | H | 3-benzo[1,3]dioxol-5-yl | methyl |
| 183 | 4-fluorophenyl | H | pyridin-2-yl | methyl |
| 184 | 4-fluorophenyl | H | pyridin-3-yl | methyl |
| 185 | 4-fluorophenyl | methyl | H | methyl |
| 186 | 4-fluorophenyl | methyl | methyl | methyl |
| 187 | 4-fluorophenyl | methyl | ethyl | methyl |
| 188 | 4-fluorophenyl | methyl | vinyl | methyl |
| 189 | 4-fluorophenyl | methyl | cyclopropyl | methyl |
| 190 | 4-fluorophenyl | methyl | cyclohexyl | methyl |
| 191 | 4-fluorophenyl | methyl | methoxymethyl | methyl |
| 192 | 4-fluorophenyl | methyl | methoxyethyl | methyl |
| 193 | 4-fluorophenyl | methyl | 1-hydroxy-1-methylethyl | methyl |
| 194 | 4-fluorophenyl | methyl | —CO$_2$H | methyl |
| 195 | 4-fluorophenyl | methyl | phenyl | methyl |
| 196 | 4-fluorophenyl | methyl | 4-fluorophenyl | methyl |
| 197 | 4-fluorophenyl | methyl | 2-aminophenyl | methyl |
| 198 | 4-fluorophenyl | methyl | 2-methylphenyl | methyl |
| 199 | 4-fluorophenyl | methyl | 4-methylphenyl | methyl |
| 200 | 4-fluorophenyl | methyl | 4-methoxyphenyl | methyl |
| 201 | 4-fluorophenyl | methyl | 4-(propanesulfonyl)phenyl | methyl |
| 202 | 4-fluorophenyl | methyl | 3-benzo[1,3]dioxol-5-yl | methyl |
| 203 | 4-fluorophenyl | methyl | pyridin-2-yl | methyl |
| 204 | 4-fluorophenyl | methyl | pyridin-3-yl | methyl |

The compounds which comprise the analogs of the second aspect of Category III can be prepared by the synthesis outline herein below in the following scheme.

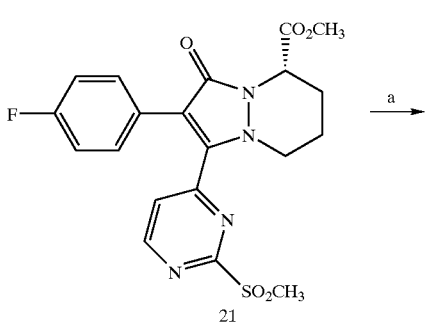

-continued

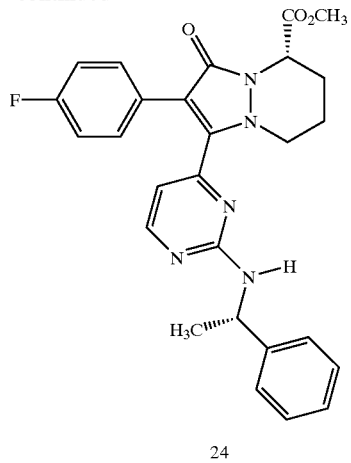

24

Reagents and conditions: (a) (S)-(-)-α-methylbenzylamine, toluene; 100° C. 4 hr.

(24): To a solution of 2-(4fluorophenyl)-1-(3-methanesulfonyl-pyrimidin-4-yl)-3-oxo-5,6, 7, 8-tetrahydro-3H-pyrazolo[1,2-a]pyridazine-5-carboxylic acid methyl ester, 21, (0.10 g, 0.22 mmol) in toluene (1.4 mL) is added (S)-(-)-α-methylbenzylamine (1.4 mL, 1.12 mmol). The reaction solution is heated to 100° C. for 4 hours after which the reaction is cooled and diluted with 1 N HCl. The resulting solution is extracted with ethyl acetate (3×25 mL), the organic layers are combined, dried, and concentrated in vacuo to afford 0.071 g (66% yield) of the desired product as a yellow solid. $^1$H NMR (300 MHz, CDCl$_3$) δ 8.22 (ddd, J=11.4, 5.1, 2.1 Hz, 1 H), 7.22–7.37 (m, 7 H), 6.97 (dt, J=8.7, 2.1 Hz, 2 H), 6.41 (ddd, J=15.6, 5.1, 2.1 Hz, 1H), 5.72–5.83 (m, 1 H), 5.2 (br s, 2 H), 5.52–5.62 (m, 1 H), 3.77 (s, 3 H), 3.47 (d, J=2.7 Hz, 1 H), 2.47–2.51 (m, 2 H), 200 (br s, 1 H), 1.41 (d, J=6.6 Hz, 3 H); APCI/MS: 487 (M+H).

EXAMPLE 10

2-(4-Fluorophenyl)-3-oxo-1-[2-(1-(S)-(phenylethylamino)pyrimidin-4-yl]-5,6,7,8-tetrahydro-3H-pyrazolo[1,2-a]pyridazine-5-carboxylic acid (25)

Preparation of 2-(4-fluorophenyl)-3-oxo-1-[2-(1-(S)-phenylethylamino)pyrimidin-4-yl]-5,6,7,8-tetrahydro-3H-pyrazolo[1,2-a]pyridazine-5-carboxylic acid (25): To a solution of Preparation of 2-(4-fluorophenyl)-3-oxo-1-[2-(S)-(1-phenylethylamino)pyrimidin-4-yl]-5,6,7,8-tetrahydro-3H-pyrazolo[1,2-a]pyridazine-5-carboxylic acid methyl ester, 24, (0.066 g, 0.14 mmol) in methanol (2 mL) and water (2 mL) is added LiOH (0.033 g, 1.36 mmol). The mixture is stirred at room temperature for 3 hours then diluted with 1 N HCl (25 mL) after which the solution is extracted with ethyl acetate (3×50 mL). The combined organic layers are washed with brine, dried, and concentrated in vacuo to afford 0.043 g (65% yield) of the desired product as a yellow solid. $^1$H NMR (300 MHz, CDCl$_3$) δ 8.13–8.19 (m, 1 H), 7.22–7.34 (m, 7 H), 6.97 (t, J=8.7 Hz, 2 H), 6.34 (dd, J=15.3, 5.1 Hz, 1 H), 5.11–5.24 (m, 2 H), 3.56 (br s, 1 H), 2.96 (br s, 1 H), 2.52–2.64 (m, 2 H), 1.79–1.96 (m, 2 H), 1.57 (d, J=6.9 Hz, 3 H): ESI/MS: 474 (M+H).

2-(4-Fluorophenyl)-3-oxo-1-[2-(1-(S)-methyl-methoxyethylamino)pyrimidin-4-yl]-5,6,7,8-tetrahydro-3H-pyrazolo[1,2-a]pyridazine-5-carboxylic acid methyl ester: $^1$H NMR (300 MHz, CDCl$_3$) δ 8.25 (d, J=5.1 Hz, 1 H), 7.43 (dd, J=9.0, 0.7 Hz, 2 H), 6.99 (t, J=9.0 Hz, 2 H), 6.44 (d, J=5.1 Hz, 1 H), 5.50–5.54 (m, 1 H), 5.26 (d, J=3.6 Hz, 1 H), 4.15–4.25 (m, 2 H), 3.76 (s, 3 H), 3.37–3.47 (m, 4 H), 2.95–3.06 (m, 1 H), 2.51–2.62 (m, 1 H), 1.92–2.02 (m, 3 H), 1.23–1.30 (m, 3 H); ESI/MS: 456 (M+H).

The third aspect of Category III analogs according to the present invention capable of inhibiting release of inflammatory cytokines relates to compounds comprising a 5,6,7,8-tetrahydro-pyrazolo[1,2-a]-pyridazin-1-one scaffold having the formula:

Reagents and conditions: (b) LiOH, MeOH/water; rt 3 hr.

EXAMPLE 9

2-(4-Fluorophenyl)-3-oxo-1-[2-(1-(S)-(phenylethylamino)pyrimidin-4-yl]-5,6,7,8-tetrahydro-3H-pyrazolo[1,2-a]pyridazine-5-carboxylic acid methyl ester (24)

Preparation of 2-(4-fluorophenyl)-3-oxo-1-[2-(1-(S)-phenylethylamino)pyrimidin-4-yl]-5,6,7,8-tetrahydro-3H-pyrazolo[1,2-a]pyridazine-5-carboxylic acid methyl ester

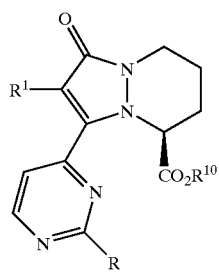

wherein R is an ether moiety of the formula: —OR³. Table VI describes the various values of R, R¹, R¹⁰

TABLE VI

| No. | R¹⁰ | R¹ | R |
|---|---|---|---|
| 205 | H | 4-fluorophenyl | phenoxy |
| 206 | H | 4-fluorophenyl | 2-fluorophenoxy |
| 207 | H | 4-fluorophenyl | 3-fluorophenoxy |
| 208 | H | 4-fluorophenyl | 4-fluorophenoxy |
| 209 | H | 4-fluorophenyl | 2,6-difluorophenoxy |
| 210 | H | 4-fluorophenyl | 2-cyanophenoxy |
| 211 | H | 4-fluorophenyl | 3-cyanophenoxy |
| 212 | H | 4-fluorophenyl | 2-trifluoromethylphenoxy |
| 213 | H | 4-fluorophenyl | 4-trifluoromethylphenoxy |
| 214 | H | 4-fluorophenyl | 2-methylphenoxy |
| 215 | H | 4-fluorophenyl | 4-methylphenoxy |
| 216 | H | 4-fluorophenyl | 2,4-dimethylphenoxy |
| 217 | H | 4-fluorophenyl | 3-N-acetylaminophenoxy |
| 218 | H | 4-fluorophenyl | 2-methoxyphenoxy |
| 219 | H | 4-fluorophenyl | 4-methoxyphenoxy |
| 220 | H | 4-fluorophenyl | 3-benzo[1,3]dioxol-5-yl |
| 221 | methyl | 4-fluorophenyl | phenoxy |
| 222 | methyl | 4-fluorophenyl | 2-fluorophenoxy |
| 223 | methyl | 4-fluorophenyl | 3-fluorophenoxy |
| 224 | methyl | 4-fluorophenyl | 4-fluorophenoxy |
| 225 | methyl | 4-fluorophenyl | 2,6-difluorophenoxy |
| 226 | methyl | 4-fluorophenyl | 2-cyanophenoxy |
| 227 | methyl | 4-fluorophenyl | 3-cyanophenoxy |
| 228 | methyl | 4-fluorophenyl | 2-trifluoromethylphenoxy |
| 229 | methyl | 4-fluorophenyl | 4-trifluoromethylphenoxy |
| 230 | methyl | 4-fluorophenyl | 2-methylphenoxy |
| 231 | methyl | 4-fluorophenyl | 4-methylphenoxy |
| 232 | methyl | 4-fluorophenyl | 2,4-dimethylphenoxy |
| 233 | methyl | 4-fluorophenyl | 3-N-acetylaminophenoxy |
| 234 | methyl | 4-fluorophenyl | 2-methoxyphenoxy |
| 235 | methyl | 4-fluorophenyl | 4-methoxyphenoxy |
| 236 | methyl | 4-fluorophenyl | 3-benzo[1,3]dioxol-5-yl |

The compounds which comprise the third aspect of Category III analogs can be prepared outlined in the following scheme.

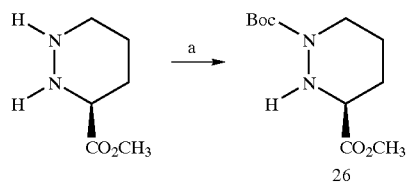

Reagents and conditions: (a) (Boc)₂O, TEA, CH₂Cl₂; rt, 12 hr.

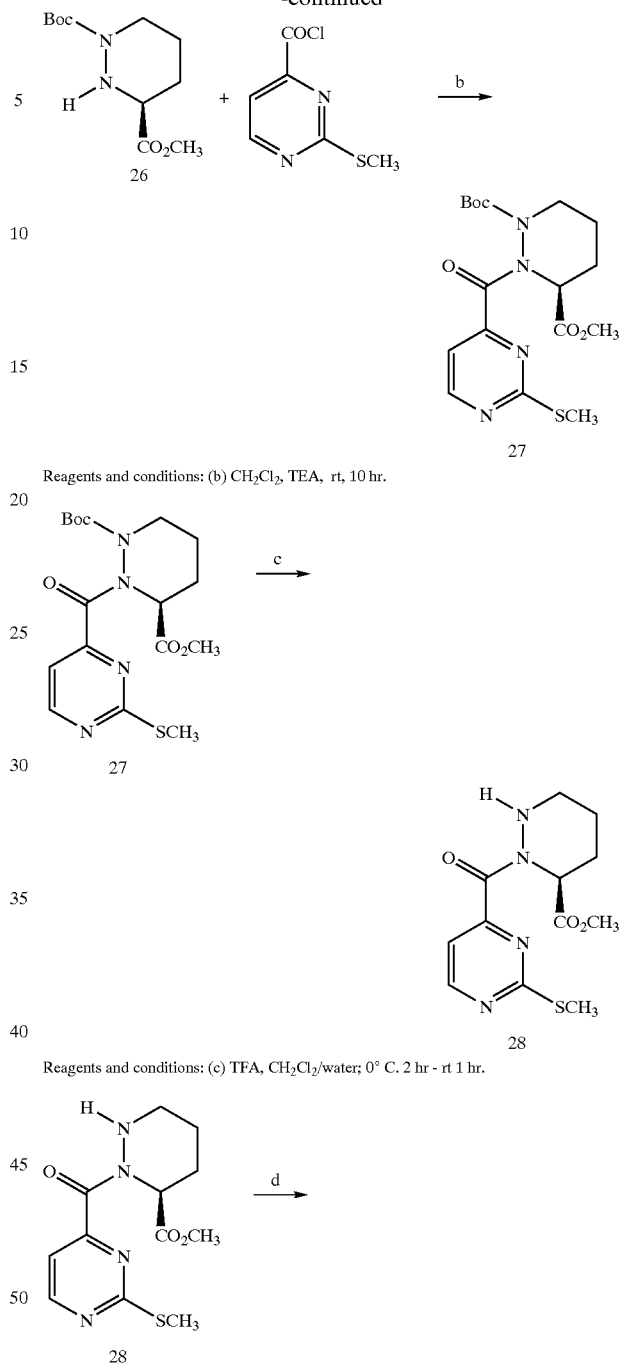

Reagents and conditions: (b) CH₂Cl₂, TEA, rt, 10 hr.

Reagents and conditions: (c) TFA, CH₂Cl₂/water; 0° C. 2 hr - rt 1 hr.

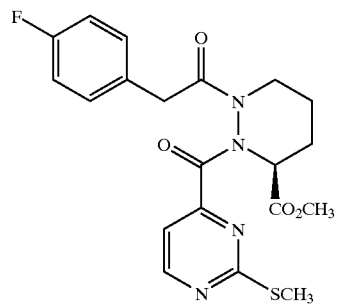

Reagents and conditions: (d) TEA, CH₂Cl₂; rt 12 hr.

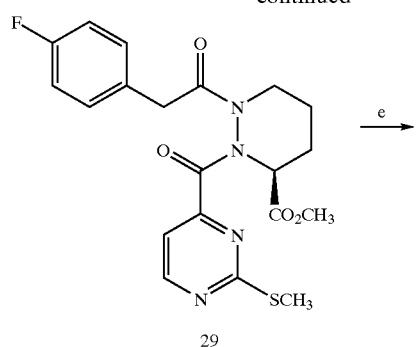

29

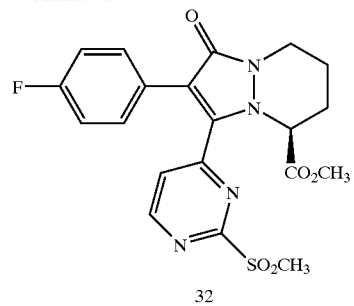

Reagents and conditions: (g) Oxone®, THF/MeOH/water; rt 5 hr.

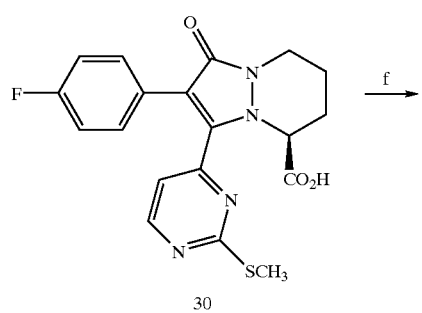

30

Reagents and conditions: (e) NaOH, MeOH; rt 15 hr.

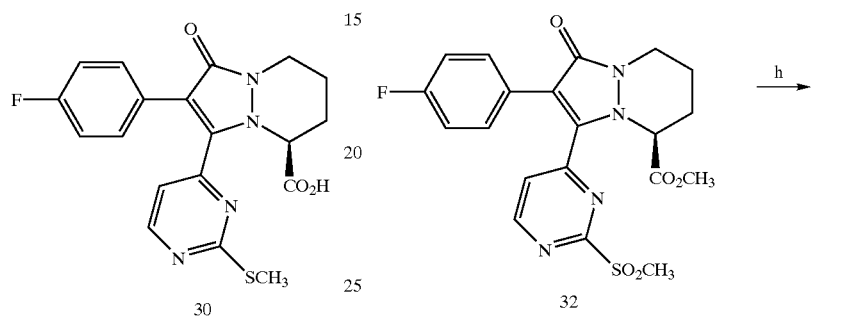

Reagents and conditions: (h) phenol, NaOH, THF; rt 8 hr.

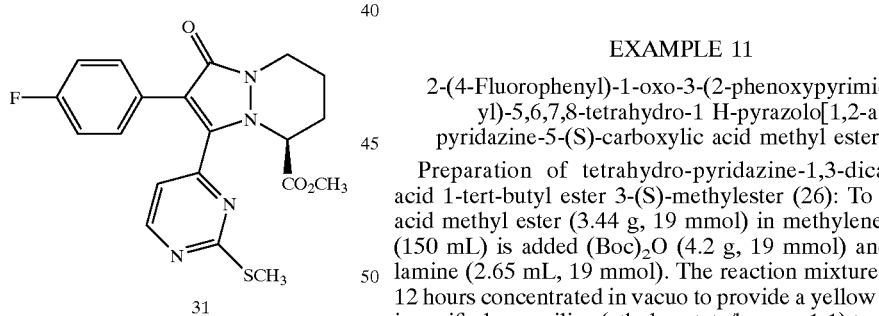

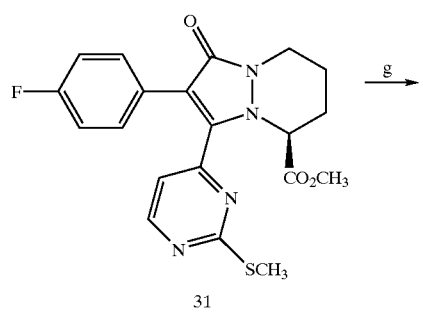

Reagents and conditions: (f) CH$_2$N$_2$, ET$_2$O/EtOAc; rt 5 min.

EXAMPLE 11

2-(4-Fluorophenyl)-1-oxo-3-(2-phenoxypyrimidin-4-yl)-5,6,7,8-tetrahydro-1 H-pyrazolo[1,2-a]pyridazine-5-(S)-carboxylic acid methyl ester (33)

Preparation of tetrahydro-pyridazine-1,3-dicarboxylic acid 1-tert-butyl ester 3-(S)-methylester (26): To piperazic acid methyl ester (3.44 g, 19 mmol) in methylene chloride (150 mL) is added (Boc)$_2$O (4.2 g, 19 mmol) and triethylamine (2.65 mL, 19 mmol). The reaction mixture is stirred 12 hours concentrated in vacuo to provide a yellow oil which is purified over silica (ethyl acetate/hexane 1:1) to afford 4.5 g (98% yield) of the desired product as a light yellow oil.

Preparation of 2-(2-methylsulfanylpyrimidine-4-carbonyl)-tetrahydropyridazine-1,3-dicarboxylic acid 1-tert-butyl 3-(S)-methylester (27): To a solution of tetrahydro-pyridazine-1,3-dicarboxylic acid 1-tert-butyl ester 3-(S)-methylester, 26, (3.91 g, 15.9 mmol) in methylene chloride (200 mL) is added 2-methanesulfanylpyrimidine-4-carbonyl chloride, 16, (3.32 g, 17.6 mmol) and triethylamine (3.5 mL, 25.3 mmol) such that the pH is approximately neutral. The resulting mixture is stirred for 10 hours at room temperature and the mixture washed with water (100 mL), brine (100 mL), dried and concentrated in vacuo to afford an oil which is purified over silica (ethyl acetate/hexane 1:1) to afford 5.22 g (83% yield) of the desired product as a yellow oil.

Preparation of 2-(2-methylsulfanylpyrimidine-4-carbonyl)-tetrahydropyridazine-1,3-dicarboxylic acid 3-(S)-methylester (28): To a solution of 2-(2-methylsulfanylpyrimidine-4-carbonyl)-tetrahydropyridazine-1,3-dicarboxylic acid 1-tert-butyl 3-(S)-methylester, 27, (7 g, 17.6 mmol) in methylene chloride (50 mL) is added trifluoroacetic acid (50 mL) at ) ° C. The reaction is stirred for 2 hours in the cold, 1 hour at room temperature, then concentrated in vacuo to a residue which can be taken up in toluene and re-concentrated to afford 7.2 g (100% yield) of the desired yield as the trifluoroacetate salt as a yellow oil which is used without further purification.

Preparation of 1-[2-(4-fluorophenyl)-2-oxo-ethyl]-2-(2-methylsulfanylpyrimmidin-4-carbonyl)-hexahydropyridazine-3-(S)-carboxylic acid (29): To a solution of 2-(2-methylsulfanyl-pyrimidine-4-carbonyl)-tetrahydropyridazine-1,3-dicarboxylic acid 3-(S)-methylester, 28, (7.2 g, 17.6 mmol) in methylene chloride (150 mL) is added 4-fluorophenylacetyl chloride (3 g, 17.6 mmol) and triethylamine (3.65 mL, 26.4 mmol). The resulting mixture is stirred for 12 hours then concentrated in vacuo to afford a brown oil. The crude residue is purified by prep HPLC to afford 5.33 g (70% yield) of the desired product as a yellow oil.

Preparation of 2-(4-fluorophenyl)-3-(2-methylsulfanylpyrimidin-4-yl)-1-oxo-5,6,7,8-tetrahydro-1H-pyrazolo[1,2-a]pyridazine-5-(S)-carboxylic acid (30): To a solution of 1-[2-(4-fluorophenyl)-2-oxo-ethyl]-2-(2-methylsulfanylpyrimmidin-4-carbonyl)-hexahydropyridazine-3-(S)-carboxylic acid, 29, (1 g) in methanol (170 mL) is added NaOH (0.23 g, 5.8 mmol). The resulting mixture is stirred for 15 hours and the mixture is concentrated in vacuo to provide a residue which is dissolved in water (150 mL). The solution is acidified to pH 1 with 3 N HCl and extracted with ethyl acetate (300 mL). The organic layer is concentrated in vacuo and the resulting crude material is purified by prep HPLC to afford 7.0 g (76% yield) of the desired product as a cream-colored solid.

Preparation of 2-(4-fluorophenyl)-3-(2-methylsulfanylpyrimidin-4-yl)-1-oxo-5,6,7,8-tetrahydro-1H-pyrazolo[1,2-a]pyridazine-5-(S)-carboxylic acid methyl ester (31): To a solution of 2-(4-fluorophenyl)-3-(2-methylsulfanylpyrimidin-4-yl)-1-oxo-5,6,7,8-tetrahydro-1H-pyrazolo[1,2-a]pyridazine-5-carboxylic acid, 30, in diethyl ether/ethyl acetate (2.5:1, 7o mL) is added freshly generated diazomethane in diethyl ether (5 mL). The reaction is stirred for 5 minutes then quenched by the addition of HOAc (0.5 mL). The resulting solution is washed with NaHCO$_3$, brine, dried, and concentrated in vacuo to afford 1 g (98% yield) of the desired product as a light yellow solid.

Preparation of 2-(4-fluorophenyl)-3-(2-methanesulfonylpyrimidin-4-yl)-1-oxo-5,6,7,8-tetrahydro-1H-pyrazolo[1,2-a]pyridazine-5-(S)-carboxylic acid methyl ester (32): To a solution of 2-(4-fluorophenyl)-3-(2-methylsulfanylpyrimidin-4-yl)-1-oxo-5,6,7,8-tetrahydro-1H-pyrazolo[1,2-a]pyridazine-5-carboxylic acid methyl ester, 31, (0.48 g, 1.16 mmol) 1:1 THF/methanol (50 mL) is added Oxone® (2.14 g, 3.5 mmol) in water (50 mL). The reaction mixture is stirred for 5 minutes at room temperature, reduced in volume in vacuo to about 25 mL and ethyl acetate (200 mL) is added. The organic phase is treated with NaHCO$_3$, brine, dried, and concentrated in vacuo to afford 0.5 g of the desired product as a yellow solid.

Preparation of 2-(4-fluorophenyl)-3-(2-phenoxypyrimidin-4-yl)-1-oxo-5,6,7,8-tetrahydro-1H-pyrazolo[1,2-a]pyridazine-5-(S)-carboxylic acid methyl ester (33): NaOH (0.112 g, 2.8 mmol) is added to a solution of phenol (0.316 g, 3.36 mmol) in THF (100 mL). 2-(4-Fluorophenyl)-3-(2-methanesulfonylpyrimidin-4-yl)-1-oxo-5,6,7,8-tetrahydro-1H-pyrazolo[1,2-a]pyridazine-5-carboxylic acid methyl ester, 32, (0.5 g) is dissolved in THF (50 mL) and added dropwise to the solution over 5 minutes. The resulting mixture is stirred at room temperature for 8 hours after which water (20 mL) is added. The solution is extracted with ethyl acetate (100 mL the organic layer washed with brine (50 mL) and concentrated in vacuo to afford 0.278 g (54% yield) of the desired product as a yellow solid. $^1$H NMR (300 MHz, CDCl$_3$) δ 1.75 (m, 2 H), 1.97 (m 1 H), 2.42 (d, J=12.8 Hz, 1 H), 3.27 (m, 1 H), 3.27 (m, 1 H), 3.6 (s, 3 H), 4.5 (br d, J=12.8 Hz, 1 H), 5.25 (m, 1 H), 6.87 (d, J=5.7 Hz, 1 H), 7.05 (m, 2H), 7.23 (m, 2 H), 7.35 (m, 3 H), 7.52 (m, 2 H), 8.42 (d, J=5.7 Hz, 1 H): exact mass calc. for C$_{25}$H$_{21}$FN$_4$O$_4$ 460.46, MS-ESI (M+1) 461.

The fourth aspect of Category III analogs according to the present invention capable of inihibiting release of inflammatory cytokines relates to compounds comprising a 5,6,7,8-tetrahydro-pyrazolo[1,2-a]-pyridazin-1-one scaffold having the formula:

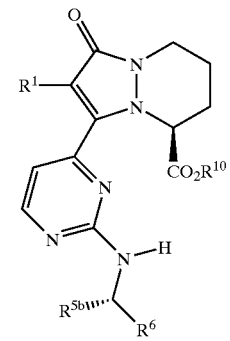

wherein R units are amines having the formula —NH [CHR$^{5b}$]R$^6$, and R$^1$, R$^{5b}$, R$^6$, and R$^{10}$ are described herein below in Table VII. The stereochemistry of R$^{5b}$ is the configuration shown when R$^{5b}$ is not hydrogen

TABLE VII

| No. | R$^1$ | R$^{5b}$ | R$^6$ | R$^{10}$ |
|---|---|---|---|---|
| 237 | 4-fluorophenyl | H | H | H |
| 238 | 4-fluorophenyl | H | methyl | H |
| 239 | 4-fluorophenyl | H | ethyl | H |
| 240 | 4-fluorophenyl | H | vinyl | H |
| 241 | 4-fluorophenyl | H | cyclopropyl | H |
| 242 | 4-fluorophenyl | H | cyclohexyl | H |
| 243 | 4-fluorophenyl | H | methoxymethyl | H |
| 244 | 4-fluorophenyl | H | methoxyethyl | H |
| 245 | 4-fluorophenyl | H | 1-hydroxy-1-methylethyl | H |
| 246 | 4-fluorophenyl | H | —CO$_2$H | H |
| 247 | 4-fluorophenyl | H | phenyl | H |
| 248 | 4-fluorophenyl | H | 4-fluorophenyl | H |
| 249 | 4-fluorophenyl | H | 2-aminophenyl | H |
| 250 | 4-fluorophenyl | H | 2-methylphenyl | H |
| 251 | 4-fluorophenyl | H | 4-methylphenyl | H |
| 252 | 4-fluorophenyl | H | 4-methoxyphenyl | H |
| 253 | 4-fluorophenyl | H | 4-(propanesulfonyl)phenyl | H |
| 254 | 4-fluorophenyl | H | 3-benzo[1,3]dioxol-5-yl | H |
| 255 | 4-fluorophenyl | H | pyridin-2-yl | H |
| 256 | 4-fluorophenyl | H | pyridin-3-yl | H |
| 257 | 4-fluorophenyl | methyl | H | H |
| 258 | 4-fluorophenyl | methyl | methyl | H |
| 259 | 4-fluorophenyl | methyl | ethyl | H |
| 260 | 4-fluorophenyl | methyl | vinyl | H |
| 261 | 4-fluorophenyl | methyl | cyclopropyl | H |

TABLE VII-continued

| No. | R¹ | R⁵ᵇ | R⁶ | R¹⁰ |
|---|---|---|---|---|
| 262 | 4-fluorophenyl | methyl | cyclohexyl | H |
| 263 | 4-fluorophenyl | methyl | methoxymethyl | H |
| 264 | 4-fluorophenyl | methyl | methoxyethyl | H |
| 265 | 4-fluorophenyl | methyl | 1-hydroxy-1-methylethyl | H |
| 266 | 4-fluorophenyl | methyl | —CO₂H | H |
| 267 | 4-fluorophenyl | methyl | phenyl | H |
| 268 | 4-fluorophenyl | methyl | 4-fluorophenyl | H |
| 269 | 4-fluorophenyl | methyl | 2-aminophenyl | H |
| 270 | 4-fluorophenyl | methyl | 2-methylphenyl | H |
| 271 | 4-fluorophenyl | methyl | 4-methylphenyl | H |
| 272 | 4-fluorophenyl | methyl | 4-methoxyphenyl | H |
| 273 | 4-fluorophenyl | methyl | 4-(propanesulfonyl)phenyl | H |
| 274 | 4-fluorophenyl | methyl | 3-benzo[1,3]dioxol-5-yl | H |
| 275 | 4-fluorophenyl | methyl | pyridin-2-yl | H |
| 276 | 4-fluorophenyl | methyl | pyridin-3-yl | H |
| 277 | 4-fluorophenyl | H | H | methyl |
| 278 | 4-fluorophenyl | H | methyl | methyl |
| 279 | 4-fluorophenyl | H | ethyl | methyl |
| 280 | 4-fluorophenyl | H | vinyl | methyl |
| 281 | 4-fluorophenyl | H | cyclopropyl | methyl |
| 282 | 4-fluorophenyl | H | cyclohexyl | methyl |
| 283 | 4-fluorophenyl | H | methoxymethyl | methyl |
| 284 | 4-fluorophenyl | H | methoxyethyl | methyl |
| 285 | 4-fluorophenyl | H | 1-hydroxy-1-methylethyl | methyl |
| 286 | 4-fluorophenyl | H | —CO₂H | methyl |
| 287 | 4-fluorophenyl | H | phenyl | methyl |
| 288 | 4-fluorophenyl | H | 4-fluorophenyl | methyl |
| 289 | 4-fluorophenyl | H | 2-aminophenyl | methyl |
| 290 | 4-fluorophenyl | H | 2-methylphenyl | methyl |
| 291 | 4-fluorophenyl | H | 4-methylphenyl | methyl |
| 292 | 4-fluorophenyl | H | 4-methoxyphenyl | methyl |
| 293 | 4-fluorophenyl | H | 4-(propanesulfonyl)phenyl | methyl |
| 294 | 4-fluorophenyl | H | 3-benzo[1,3]dioxol-5-yl | methyl |
| 295 | 4-fluorophenyl | H | pyridin-2-yl | methyl |
| 296 | 4-fluorophenyl | H | pyridin-3-yl | methyl |
| 297 | 4-fluorophenyl | methyl | H | methyl |
| 298 | 4-fluorophenyl | methyl | methyl | methyl |
| 299 | 4-fluorophenyl | methyl | ethyl | methyl |
| 300 | 4-fluorophenyl | methyl | vinyl | methyl |
| 301 | 4-fluorophenyl | methyl | cyclopropyl | methyl |
| 302 | 4-fluorophenyl | methyl | cyclohexyl | methyl |
| 303 | 4-fluorophenyl | methyl | methoxymethyl | methyl |
| 304 | 4-fluorophenyl | methyl | methoxyethyl | methyl |
| 305 | 4-fluorophenyl | methyl | 1-hydroxy-1-methylethyl | methyl |
| 306 | 4-fluorophenyl | methyl | —CO₂H | methyl |
| 307 | 4-fluorophenyl | methyl | phenyl | methyl |
| 308 | 4-fluorophenyl | methyl | 4-fluorophenyl | methyl |
| 309 | 4-fluorophenyl | methyl | 2-aminophenyl | methyl |
| 310 | 4-fluorophenyl | methyl | 2-methylphenyl | methyl |
| 311 | 4-fluorophenyl | methyl | 4-methylphenyl | methyl |
| 312 | 4-fluorophenyl | methyl | 4-methoxyphenyl | methyl |
| 313 | 4-fluorophenyl | methyl | 4-(propanesulfonyl)phenyl | methyl |
| 314 | 4-fluorophenyl | methyl | 3-benzo[1,3]dioxol-5-yl | methyl |
| 315 | 4-fluorophenyl | methyl | pyridin-2-yl | methyl |
| 316 | 4-fluorophenyl | methyl | pyridin-3-yl | methyl |

The compounds which comprise the analogs of the fourth aspect of Category III can be prepared by the synthesis outline herein below in the following scheme starting with intermediate 32.

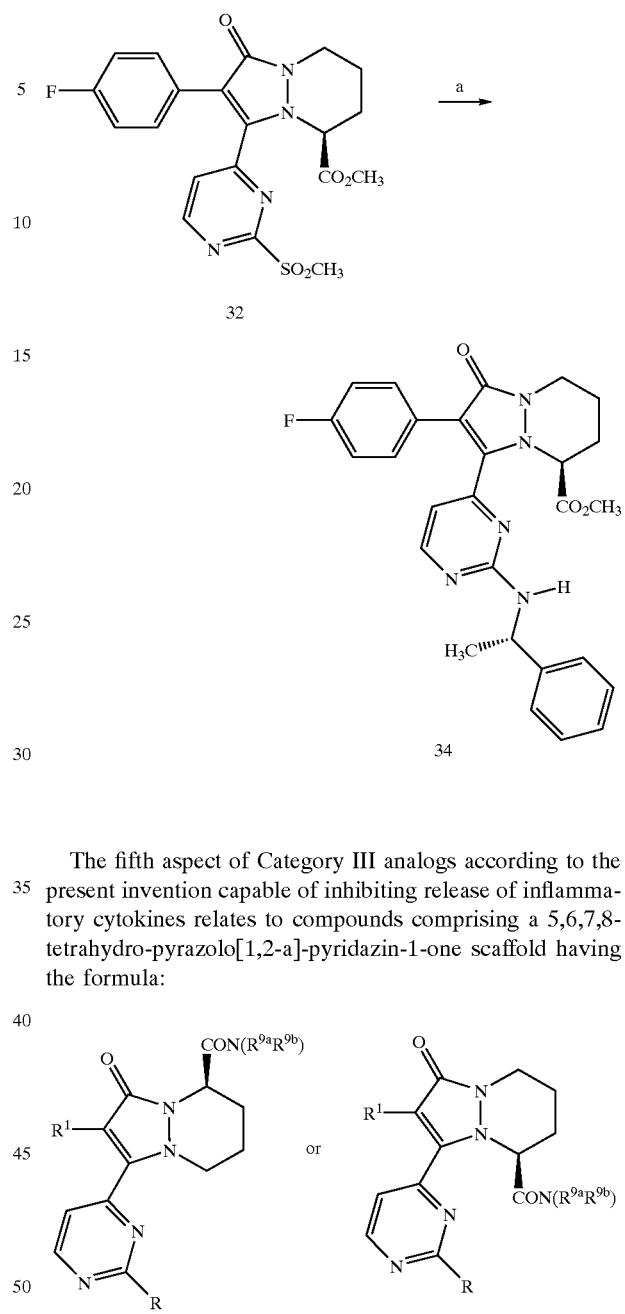

The fifth aspect of Category III analogs according to the present invention capable of inhibiting release of inflammatory cytokines relates to compounds comprising a 5,6,7,8-tetrahydro-pyrazolo[1,2-a]-pyridazin-1-one scaffold having the formula:

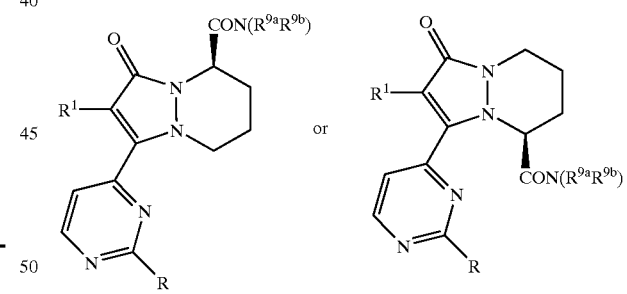

wherein R, R¹, R⁹ᵃ, and R⁹ᵇ are defined herein below in Table VIII.

TABLE VIII

| No. | R¹ | R | R⁹ᵃ | R⁹ᵇ |
|---|---|---|---|---|
| 317 | 4-fluorophenyl | phenoxy | H | H |
| 318 | 4-fluorophenyl | 2-fluorophenoxy | H | H |
| 319 | 4-fluorophenyl | 3-fluorophenoxy | H | H |
| 320 | 4-fluorophenyl | 4-fluorophenoxy | H | H |
| 321 | 4-fluorophenyl | 2,6-difluorophenoxy | H | H |
| 322 | 4-fluorophenyl | 2-cyanophenoxy | H | H |

TABLE VIII-continued

| No. | R¹ | R | R⁹ᵃ | R⁹ᵇ |
|---|---|---|---|---|
| 323 | 4-fluorophenyl | 3-cyanophenoxy | H | H |
| 324 | 4-fluorophenyl | 2-trifluoromethylphenoxy | H | H |
| 325 | 4-fluorophenyl | 4-trifluoromethylphenoxy | H | H |
| 326 | 4-fluorophenyl | 2-methylphenoxy | H | H |
| 327 | 4-fluorophenyl | 4-methylphenoxy | H | H |
| 328 | 4-fluorophenyl | 2,4-dimethylphenoxy | H | H |
| 329 | 4-fluorophenyl | 3-N-acetylaminophenoxy | H | H |
| 330 | 4-fluorophenyl | 2-methoxyphenoxy | H | H |
| 331 | 4-fluorophenyl | 4-methoxyphenoxy | H | H |
| 332 | 4-fluorophenyl | 3-benzo[1,3]dioxol-5-yl | H | H |
| 333 | 4-fluorophenyl | phenoxy | methyl | methyl |
| 334 | 4-fluorophenyl | 2-fluorophenoxy | methyl | methyl |
| 335 | 4-fluorophenyl | 3-fluorophenoxy | methyl | methyl |
| 336 | 4-fluorophenyl | 4-fluorophenoxy | methyl | methyl |
| 337 | 4-fluorophenyl | 2,6-difluorophenoxy | methyl | methyl |
| 338 | 4-fluorophenyl | 2-cyanophenoxy | methyl | methyl |
| 339 | 4-fluorophenyl | 3-cyanophenoxy | methyl | methyl |
| 340 | 4-fluorophenyl | 2-trifluoromethylphenoxy | methyl | methyl |
| 341 | 4-fluorophenyl | 4-trifluoromethylphenoxy | methyl | methyl |
| 342 | 4-fluorophenyl | 2-methylphenoxy | methyl | methyl |
| 343 | 4-fluorophenyl | 4-methylphenoxy | methyl | methyl |
| 344 | 4-fluorophenyl | 2,4-dimethylphenoxy | methyl | methyl |
| 345 | 4-fluorophenyl | 3-N-acetylaminophenoxy | methyl | methyl |
| 346 | 4-fluorophenyl | 2-methoxyphenoxy | methyl | methyl |
| 347 | 4-fluorophenyl | 4-methoxyphenoxy | methyl | methyl |
| 348 | 4-fluorophenyl | 3-benzo[1,3]dioxol-5-yl | methyl | methyl |
| 349 | 4-fluorophenyl | 1-(S)-phenylethylamino | H | H |
| 350 | 4-fluorophenyl | 1-(S)-(4-fluorophenyl)ethylamino | H | H |
| 351 | 4-fluorophenyl | 1-(S)-(2-aminophenyl)ethylamino | H | H |
| 352 | 4-fluorophenyl | 1-(S)-(2-methylphenyl)ethylamino | H | H |
| 353 | 4-fluorophenyl | 1-(S)-(4-methylphenyl)ethylamino | H | H |
| 354 | 4-fluorophenyl | 1-(S)-(4-methoxyphenyl)ethylamino | H | H |
| 355 | 4-fluorophenyl | 1-(S)-(4-propanesulfonylphenyl)ethylamino | H | H |
| 356 | 4-fluorophenyl | 1-(S)-(3-benzo[1,3]dioxol-5-yl)ethylamino | H | H |
| 357 | 4-fluorophenyl | 1-(S)-(pyridin-2-yl)ethylamino | H | H |
| 358 | 4-fluorophenyl | 1-(S)-(pyridin-3-yl)ethylamino | H | H |
| 359 | 4-fluorophenyl | methylamino | H | H |
| 360 | 4-fluorophenyl | ethylamino | H | H |
| 361 | 4-fluorophenyl | propylamino | H | H |
| 362 | 4-fluorophenyl | cyclopropylamino | H | H |
| 363 | 4-fluorophenyl | cyclopropylmethylamino | H | H |
| 364 | 4-fluorophenyl | tert-butylamino | H | H |
| 365 | 4-fluorophenyl | 1-(S)-(cyclopropyl)ethylamino | H | H |
| 366 | 4-fluorophenyl | 1-(S)-(cyclopropylmethyl)ethylamino | H | H |
| 367 | 4-fluorophenyl | 1-(R)-(α)-(carboxy)benzylamino | H | H |
| 368 | 4-fluorophenyl | 1-(S)-(α)-(methyl)benzylamino | H | H |
| 369 | 4-fluorophenyl | 1-(S)-phenylethylamino | methyl | methyl |
| 370 | 4-fluorophenyl | 1-(S)-(4-fluorophenyl)ethylamino | methyl | methyl |
| 371 | 4-fluorophenyl | 1-(S)-(2-aminophenyl)ethylamino | methyl | methyl |
| 372 | 4-fluorophenyl | 1-(S)-(2-methylphenyl)ethylamino | methyl | methyl |
| 373 | 4-fluorophenyl | 1-(S)-(4-methylphenyl)ethylamino | methyl | methyl |
| 374 | 4-fluorophenyl | 1-(S)-(4-methoxyphenyl)ethylamino | methyl | methyl |
| 375 | 4-fluorophenyl | 1-(S)-(4-propanesulfonylphenyl)ethylamino | methyl | methyl |
| 376 | 4-fluorophenyl | 1-(S)-(3-benzo[1,3]dioxol-5-yl)ethylamino | methyl | methyl |
| 377 | 4-fluorophenyl | 1-(S)-(pyridin-2-yl)ethylamino | methyl | methyl |
| 378 | 4-fluorophenyl | 1-(S)-(pyridin-3-yl)ethylamino | methyl | methyl |
| 379 | 4-fluorophenyl | methylamino | methyl | methyl |
| 380 | 4-fluorophenyl | ethylamino | methyl | methyl |
| 381 | 4-fluorophenyl | propylamino | methyl | methyl |
| 382 | 4-fluorophenyl | cyclopropylamino | methyl | methyl |
| 383 | 4-fluorophenyl | cyclopropylmethylamino | methyl | methyl |
| 384 | 4-fluorophenyl | tert-butylamino | methyl | methyl |
| 385 | 4-fluorophenyl | 1-(S)-(cyclopropyl)ethylamino | methyl | methyl |
| 386 | 4-fluorophenyl | 1-(S)-(cyclopropylmethyl)ethylamino | methyl | methyl |
| 387 | 4-fluorophenyl | 1-(R)-(α)-(carboxy)benzylamino | methyl | methyl |
| 388 | 4-fluorophenyl | 1-(S)-(α)-(methyl)benzylamino | methyl | methyl |

Another iteration of this aspect relates to compounds wherein $R^{9a}$ and $R^{9b}$ are taken together to form a carbocyclic or heterocyclic ring comprising from 3 to 7 atoms. Table IX describes compounds encompassed by this iteration of the fifth aspect of Category III.

TABLE IX

| No. | $R^1$ | R | $R^{9a}$–$R^{9b}$ ring |
|---|---|---|---|
| 389 | 4-fluorophenyl | phenoxy | morpholin-4-yl |
| 390 | 4-fluorophenyl | 2-fluorophenoxy | morpholin-4-yl |
| 391 | 4-fluorophenyl | 3-fluorophenoxy | morpholin-4-yl |
| 392 | 4-fluorophenyl | 4-fluorophenoxy | morpholin-4-yl |
| 393 | 4-fluorophenyl | 3-cyanophenoxy | morpholin-4-yl |
| 394 | 4-fluorophenyl | 4-methylphenoxy | morpholin-4-yl |
| 395 | 4-fluorophenyl | 3-N-acetylaminophenoxy | morpholin-4-yl |
| 396 | 4-fluorophenyl | 4-methoxyphenoxy | morpholin-4-yl |
| 397 | 4-fluorophenyl | phenoxy | piperadin-1-yl |
| 398 | 4-fluorophenyl | 2-fluorophenoxy | piperadin-1-yl |
| 399 | 4-fluorophenyl | 3-fluorophenoxy | piperadin-1-yl |
| 400 | 4-fluorophenyl | 4-fluorophenoxy | piperadin-1-yl |
| 401 | 4-fluorophenyl | 3-cyanophenoxy | piperadin-1-yl |
| 402 | 4-fluorophenyl | 4-methylphenoxy | piperadin-1-yl |
| 403 | 4-fluorophenyl | 3-N-acetylaminophenoxy | piperadin-1-yl |
| 404 | 4-fluorophenyl | 4-methoxyphenoxy | piperadin-1-yl |
| 405 | 4-fluorophenyl | phenoxy | piperazin-1-yl |
| 406 | 4-fluorophenyl | 2-fluorophenoxy | piperazin-1-yl |
| 407 | 4-fluorophenyl | 3-fluorophenoxy | piperazin-1-yl |
| 408 | 4-fluorophenyl | 4-fluorophenoxy | piperazin-1-yl |
| 409 | 4-fluorophenyl | 3-cyanophenoxy | piperazin-1-yl |
| 410 | 4-fluorophenyl | 4-methylphenoxy | piperazin-1-yl |
| 411 | 4-fluorophenyl | 3-N-acetylaminophenoxy | piperazin-1-yl |
| 412 | 4-fluorophenyl | 4-methoxyphenoxy | piperazin-1-yl |
| 413 | 4-fluorophenyl | phenoxy | cyclohexyl |
| 414 | 4-fluorophenyl | 2-fluorophenoxy | cyclohexyl |
| 415 | 4-fluorophenyl | 3-fluorophenoxy | cyclohexyl |
| 416 | 4-fluorophenyl | 4-fluorophenoxy | cyclohexyl |
| 417 | 4-fluorophenyl | 3-cyanophenoxy | cyclohexyl |
| 418 | 4-fluorophenyl | 4-methylphenoxy | cyclohexyl |
| 419 | 4-fluorophenyl | 3-N-acetylaminophenoxy | cyclohexyl |
| 420 | 4-fluorophenyl | 4-methoxyphenoxy | cyclohexyl |
| 421 | 4-fluorophenyl | 1-(S)-phenylethylamino | morpholin-4-yl |
| 422 | 4-fluorophenyl | 1-(S)-(4-fluorophenyl)ethylamino | morpholin-4-yl |
| 423 | 4-fluorophenyl | 1-(S)-(pyridin-2-yl)ethylamino | morpholin-4-yl |
| 424 | 4-fluorophenyl | 1-(S)-(pyridin-3-yl)ethylamino | morpholin-4-yl |
| 425 | 4-fluorophenyl | ethylamino | morpholin-4-yl |
| 426 | 4-fluorophenyl | propylamino | morpholin-4-yl |
| 427 | 4-fluorophenyl | cyclopropylamino | morpholin-4-yl |
| 428 | 4-fluorophenyl | cyclopropylmethylamino | morpholin-4-yl |
| 429 | 4-fluorophenyl | tert-butylamino | morpholin-4-yl |
| 430 | 4-fluorophenyl | 1-(S)-(α)-(methyl)benzylamino | morpholin-4-yl |
| 431 | 4-fluorophenyl | 1-(S)-phenylethylamino | piperadin-1-yl |
| 432 | 4-fluorophenyl | 1-(S)-(4-fluorophenyl)ethylamino | piperadin-1-yl |
| 433 | 4-fluorophenyl | 1-(S)-(pyridin-2-yl)ethylamino | piperadin-1-yl |
| 434 | 4-fluorophenyl | 1-(S)-(pyridin-3-yl)ethylamino | piperadin-1-yl |
| 435 | 4-fluorophenyl | ethylamino | piperadin-1-yl |
| 436 | 4-fluorophenyl | propylamino | piperadin-1-yl |
| 437 | 4-fluorophenyl | cyclopropylamino | piperadin-1-yl |
| 438 | 4-fluorophenyl | cyclopropylmethylamino | piperadin-1-yl |
| 439 | 4-fluorophenyl | tert-butylamino | piperadin-1-yl |
| 4402441 | 4-fluorophenyl | 1-(S)-(α)-(methyl)benzylamino | piperadin-1-yl |
| 442 | 4-fluorophenyl | 1-(S)-phenylethylamino | piperazin-1-yl |
| 443 | 4-fluorophenyl | 1-(S)-(4-fluorophenyl)ethylamino | piperazin-1-yl |
| 444 | 4-fluorophenyl | 1-(S)-(pyridin-2-yl)ethylamino | piperazin-1-yl |
| 445 | 4-fluorophenyl | 1-(S)-(pyridin-3-yl)ethylamino | piperazin-1-yl |
| 446 | 4-fluorophenyl | ethylamino | piperazin-1-yl |
| 447 | 4-fluorophenyl | propylamino | piperazin-1-yl |
| 448 | 4-fluorophenyl | cyclopropylamino | piperazin-1-yl |
| 449 | 4-fluorophenyl | cyclopropylmethylamino | piperazin-1-yl |
| 450 | 4-fluorophenyl | tert-butylamino | piperazin-1-yl |
| 451 | 4-fluorophenyl | 1-(S)-(α)-(methyl)benzylamino | piperazin-1-yl |
| 452 | 4-fluorophenyl | 1-(S)-phenylethylamino | cyclohexyl |
| 453 | 4-fluorophenyl | 1-(S)-(4-fluorophenyl)ethylamino | cyclohexyl |
| 454 | 4-fluorophenyl | 1-(S)-(pyridin-2-yl)ethylamino | cyclohexyl |
| 455 | 4-fluorophenyl | 1-(S)-(pyridin-3-yl)ethylamino | cyclohexyl |
| 456 | 4-fluorophenyl | ethylamino | cyclohexyl |
| 457 | 4-fluorophenyl | propylamino | cyclohexyl |
| 458 | 4-fluorophenyl | cyclopropylamino | cyclohexyl |
| 459 | 4-fluorophenyl | cyclopropylmethylamino | cyclohexyl |
| 460 | 4-fluorophenyl | tert-butylamino | cyclohexyl |
| 461 | 4-fluorophenyl | 1-(S)-(α)-(methyl)benzylamino | cyclohexyl |

Other compounds according to the present invention include:

2-(4-Fluorophenyl)-5-(piperazine-1-carbonyl)-3-(2-phenoxypyrimidin-4-yl)-5,6,7,8-tetrahydro-3H-pyrazolo[1,2-a]pyridazin-1-one:

2-(4-Fluorophenyl)-8-(piperazine-1-carbonyl)-3-(2-phenoxypyrimidin-4-yl)-5,6,7,8-tetrahydropyrazolo[1,2-a]pyridazin-1-one 2-(4-Fluorophenyl)-8-(morpholine-4-carbonyl)-3-(2-phenoxypyrimidin-4-yl)-5,6,7,8-tetrahydropyrazolo[1,2-a]pyridazin-1-one;

2-(4-Fluorophenyl)-5-(morpholine-4-carbonyl)-3-[2-(4-fluorophenoxy)pyrimidin-4-yl]-5,6,7,8-tetrahydropyrazolo[1,2-a]pyridazin-1-one;

2-(4-Fluorophenyl)-8-(morpholine-4-carbonyl)-3-[2-(4-fluorophenoxy)pyrimidin-4-yl]-5,6,7,8-tetrahydropyrazolo[1,2-a]pyridazin-1-one;

2-(4-Fluorophenyl)-5-(morpholine-4-carbonyl)-3-{2-[1-(S)-(α)-(methyl)benzylamino]-pyrimidin-4-yl}-5,6,7,8-tetrahydropyrazolo[1,2-a]pyridazin-1-one;

2-(4-Fluorophenyl)-8-(morpholine-4-carbonyl)-3-{2-[1-(S)-(α)-(methyl)benzylamino]-pyrimidin-4-yl}-5,6,7,8-tetrahydropyrazolo[1,2-a]pyridazin-1-one;

The analogs (compounds) of the present invention are arranged in several categories to assist the formulator in applying a rational synthetic strategy for the preparation of analogs which are not expressly exampled herein. The arrangement into categories does not imply increased or decreased efficacy for any of the compositions of matter described herein.

Compounds listed and described herein above have been found in many instances to exhibit activities ($IC_{50}$ in the cell based assay described herein below or ones which are referenced herein) at a level below 1 micromolar ($\mu M$).

The compounds of the present invention are capable of effectively blocking the production of inflammatory cytokine production from cells, which thereby allows for the mitigation, alleviation, control, abatement, retardation, or prevention of one or more disease states or syndromes which are related to the extracellular release of one or more cytokines. Inflammatory disease states include those which are related to the following non-limiting examples:

i) Interleukin-1 (IL-1): implicated as the molecule responsible for a large number of disease states, inter alia, rheumatoid arthritis, osteoarthritis, as well as other disease states which relate to connective tissue degradation.

ii) Cycloxygenase-2 (COX-2): inhibitors of cytokine release are proposed as inhibitors of inducible COX-2 expression, which has been shown to be increased by cytokines. M. K. O'Banion et al., *Proc. Natl. Acad. Sci. U.S.A.*, 89, 4888 (1998).

iii) Tumor Necrosis Factor-α (TNF-α): This pro-inflammatory cytokine is suggested as an important mediator in many disease states or syndromes, inter alia, rheumatoid arthritis, osteoarthritis, inflammatory bowel disease (IBS), septic shock, cardiopulmonary dysfunction, acute respiratory disease, and cachexia.

Each of the disease states or conditions which the formulator desires to treat may require differing levels or amounts of the compounds described herein to obtain a therapeutic level. The formulator can determine this amount by any of the known testing procedures known to the artisan.

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Related to this aspect are the various precursor of "pro-drug" forms of the analogs of the present invention. It may be desirable to formulate the compounds of the present invention as a chemical species which itself is not active against the cytokine activity described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. The term "pro-drug" relates to these species which are converted in vivo to the active pharmaceutical.

Formulations

The present invention also relates to compositions or formulations which comprise the inflammatory cytokine release-inhibiting compounds according to the present invention. In general, the compositions of the present invention comprise:

a) an effective amount of one or more bicyclic pyrazolones and derivatives thereof according to the present invention which are effective for inhibiting release of inflammatory cytokines; and b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present invention also relates to compositions or formulations which comprise a precursor or "pro-drug" form of the inflammatory cytokine release-inhibiting compounds according to the present invention. In general, these precursor-comprising compositions of the present invention comprise:

a) an effective amount of one or more derivatives of bicyclic pyrazolones according to the present invention which act to release in vivo the corresponding analog which is effective for inhibiting release of inflammatory cytokines; and b) one or more pharmaceutically acceptable excipients.

Method of Use

The present invention also relates to a method for controlling the level of one or more inflammation inducing cytokines, inter alia, interleukin-1 (IL-1), Tumor Necrosis Factor-α (TNF-α), interleukin-6 (IL-6), and interleukin-8 (IL-8) and thereby controlling, mediating, or abating disease states affected by the levels of extracellular inflammatory cytokines. The present method comprises the step of administering to a human or higher mammal an effective amount of a composition comprising one or more of the inflammatory cytokine inhibitors according to the present invention.

Because the inflammatory cytokine inhibitors of the present invention can be delivered in a manner wherein more than one site of control can be achieved, more than one disease state can be modulated at the same time. Non-limiting examples of diseases which are affected by control or inhibition of inflammatory cytokine inhibitors, thereby modulating excessive cytokine activity, include osteoarthritis, rheumatoid arthritis, diabetes, human Immunodeficiency virus (HIV) infection.

Procedures

The compounds of the present invention can be evaluated for efficacy, for example, measurements of cytokine inhibition constants, $K_1$, and $IC_{50}$ values can be obtained by any method chosen by the formulator.

Non-limiting examples of suitable assays include:
i) UV-visible substrate enzyme assay as described by L. Al Reiter, *Int. J. Peptide Protein Res.*, 43, 87–96 (1994).
ii) Fluorescent substrate enzyme assay as described by Thornberry et al., *Nature*, 356, 768–774 (1992).
iii) PBMC Cell assay as described in U.S. Pat. No. 6,204,261 B1 Batchelor et al., issued Mar. 20, 2001.

Each of the above citations is included herein by reference.

In addition, Tumor Necrosis Factor, TNF-α, inhibition can be measured by utilizing lipopolysaccharide (LPS) stimulated human monocytic cells (THP-1) as described in:
i) K. M. Mohler et al., "Protection Against a Lethal Dose of Endotoxin by an Inhibitor of Tumour Necrosis Factor Processing", *Nature*, 370, pp 218–220 (1994).
ii) U.S. Pat. No. 6,297,381 B1 Cirillo et al., issued Oct. 2, 2001, incorporated by reference and reproduced herein below in relevant portion thereof.

The inhibition of cytokine production can be observed by measuring inhibition of TNF-α in lipopolysaccharide stimulated THP cells. All cells and reagents are diluted in RPMI 1640 with phenol red and L-glutamine, supplemented with additional L-glutamine (total: 4 mM), penicillin and streptomycin (50 units/mL each) and fetal bovine serum (FBS 3%) (GIBCO, all conc. Final). Assay is performed under sterile conditions, only test compound preparation is non-sterile. Initial stock solutions are made in DMSO followed by dilution into RPMI 1640 2-fold higher than the desired final assay concentration. Confluent THP.1 cells (2×10⁶ cells/mL, final conc.; American Type Culture Company, Rockville, Md.) are added to 96 well polypropylene round bottomed culture plates (Costar 3790; sterile) containing 125 μL test compound (2-fold concentrated) or DMSO vehicle (controls, blanks). DMSO concentration should not exceed 0.2% final. Cell mixture is allowed to preincubate for 30 minutes at 37° C., 5% $CO_2$ prior to stimulation with lipopolysaccharide (LPS, 1 μg/mL final; Sigma L-2630, from *E. coli* serotype 0111B4; stored as 1 mg/mL stock in endotoxin screened diluted $H_2O$ vehicle at −80° C.). Blanks (unstimulated) receive $H_2O$ vehicle; final incubation volume is 250 μL. Incubation (4 hours) proceeds as described above. Assay is to be terminated by centrifuging plates 5 minutes at room temperature, 1600 rpm (4033 g); supernatants are then transferred to clean 96 well plates and stored at −80° C. until analyzed for human TNF-α by a commercially available ELISA kit (Biosource #KHC3015, Camarillo, Calif.). The calculated $IC_{50}$ value is the concentration of the test compound that caused a 50% decrease in the maximal TNF-α production.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound, or all enantiomeric and diasteriomeric forms or pharmaceutically acceptable salts thereof, said compound having the formula:

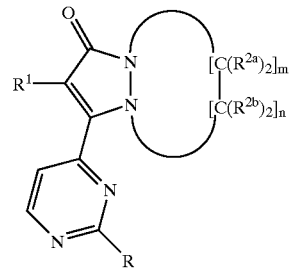

wherein R is:
a) hydrogen;
b) —O[CH₂]$_k$R³; or
c) —NR$^{4a}$R$^{4b}$;

R³ is substituted or unsubstituted $C_1$–$C_4$ alkyl, substituted or unsubstituted cyclic hydrocarbyl, substituted or unsubstituted heterocyclyl, substituted or unsubstituted aryl, substituted or unsubstituted heteroaryl; the index k is from 0 to 5;

R$^{4a}$ and R$^{4b}$ are each independently:
a) hydrogen; or
b) —[C(R$^{5a}$R$^{5b}$)]$_x$R⁶;

each R$^{5a}$ and R$^{5b}$ are independently hydrogen, —OR⁷, —N(R⁷)₂, —CO₂R⁷, —CON(R⁷)₂, $C_1$–$C_4$ linear, branched, or cyclic alkyl, and mixtures thereof; R⁶ is —OR⁷, —N(R⁷)₂, —CO₂R⁷, —CON(R⁷)₂; substituted or unsubstituted $C_1$–$C_4$ alkyl, substituted or unsubstituted aryl, or substituted or unsubstituted heteroaryl; R⁷ is hydrogen, a water-soluble cation, $C_1$–$C_4$ alkyl, or substituted or unsubstituted aryl; the index x is from 0 to 5;

R¹ is:
a) substituted or unsubstituted aryl; or
b) substituted or unsubstituted heteroaryl;

R$^{2a}$ and R$^{2b}$ units are each independently selected from the group consisting of:
a) hydrogen;
b) —O(CH₂)$_j$R⁸;
c) —(CH₂)$_j$NR$^{9a}$R$^{9b}$;
d) —(CH₂)$_j$CO₂R¹⁰;
e) —(CH₂)$_j$OCO₂R¹⁰
f) —(CH₂)$_j$CON(R¹⁰)₂;
g) two R$^{2a}$ or two R$^{2b}$ units from the same carbon atom can be taken together to form a carbonyl unit;
h) one R$^{2a}$ and one R$^{2b}$ are taken together to form a double bond;

53 i) one $R^{2a}$ and one $R^{2b}$ are taken together to form a substituted or unsubstituted ring having from 4 to 8 atoms, said ring selected from the group consisting of:
  i) carbocyclic;
  ii) heterocyclic;
  iii) aryl; and
  iv) heteroaryl;

$R^8$, $R^{9a}$, $R^{9b}$, and $R^{10}$ are each independently hydrogen, $C_1$–$C_4$ alkyl, or $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5; m is an index from 1 to 5, n is an index from 1 to 5; m+n=from 2 to 6, with the provision that m+n is not 3.

2. A compound according to claim 1 having the formula:

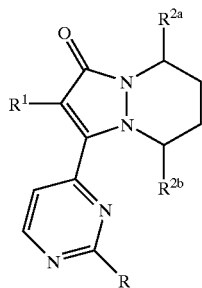

wherein R is:
  i) an ether having the formula —O[CH$_2$]$_k$R$^3$; or
  ii) an amine having the formula —NR$^{4a}$R$^{4b}$;
$R^3$ is substituted or unsubstituted aryl;
$R^{4a}$ and $R^{4b}$ are each independently:
  a) hydrogen; or
  b) —[C(R$^{5a}$R$^{5b}$)]$_x$R$^6$;
each $R^{5a}$ and $R^{5b}$ are independently hydrogen, $C_1$–$C_4$ linear, branched, or cyclic alkyl, —CO$_2$R$^7$, —CON (R$^7$); $R^6$ is substituted or unsubstituted $C_1$–$C_4$ alkyl, substituted or unsubstituted aryl; $R^7$ is hydrogen, a water-soluble cation, or $C_1$–$C_4$ alkyl; the index x is 0 to 5;
$R^1$ is selected from the group consisting of 4-fluorophenyl, 2,4-difluorophenyl, and 4-chlorophenyl;
each $R^{2a}$ or $R^{2b}$ unit is independently selected from the group consisting of:
  a) hydrogen;
  b) —O(CH$_2$)$_j$R$^8$;
  c) —(CH$_2$)$_j$NR$^{9a}$R$^{9b}$; and
  d) —(CH$_2$)$_j$CO$_2$R$^{10}$;
j is 0.

3. A compound according to claim 2 wherein $R^{2a}$ or $R^{2b}$ is —CO$_2$H, —CO$_2$CH$_3$, —CONH$_2$, or —CON(CH$_3$)$_2$.

4. A compound according to claim 2 wherein one $R^{2a}$ and one $R^{2b}$ is taken together to form a double bond.

5. A compound according to claim 2 wherein $R^{2a}$ or $R^{2b}$ has the formula —(CH$_2$)$_j$NR$^{9a}$R$^{9b}$; $R^{9a}$ and $R^{9b}$ are taken together to form a ring selected from the group consisting of morpholinyl, piperidinyl, piperazinyl, and cyclohexyl; the index j is 0.

6. A compound according to claim 2 wherein $R^1$ is 4-fluorophenyl.

7. A compound according to claim 2 wherein R is selected from the group consisting of phenoxy, 2-fluorophenoxy,

54

3-fluorophenoxy, 4-fluorophenoxy, 2,6-difluorophenoxy, 2-cyanophenoxy, 3-cyanophenoxy, 2-trifluoromethylphenoxy, 4-trifluoromethylphenoxy, 2-methylphenoxy, 4-methylphenoxy, 2,4-dimethylphenoxy, 3-N-acetylaminophenoxy, 2-methoxyphenoxy, 4-methoxyphenoxy, and 3-benzo[1,3]dioxol-5-yl.

8. A compound according to claim 2 wherein R is selected from the group consisting of 1-(S)-phenylethylamino, 1-(S)-(4-fluorophenyl)ethylamino, 1-(S)-(2-aminophenyl) ethylamino, 1-(S)-(2-methylphenyl)ethylamino, 1-(S)-(4-methylphenyl)ethylamino, 1-(S)-(4-methylphenyl) ethylamino, 1-(S)-(4-propanesulfonylphenyl)ethylamino, 1-(S)-(3-benzo[1,3]dioxol-5-yl)ethylamino, 1-(S)-(pyridin-2-yl)ethylamino, 1-(S)-(pyridin-3-yl)ethylamino, methylamino, ethylamino, propylamino, cyclopropylamino cyclopropyl-methylamino, tert-butylamino, 1-(S)-(cyclopropyl)ethylamino, 1-(S)-(cyclopropylmethyl)-ethylamino, 1-(R)-(α)-(carboxy)benzylamino, and 1-(S)-(α)-(methyl)benzylamino.

9. A compound according to claim 1 having the formula:

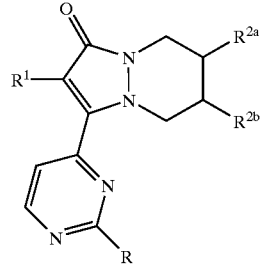

wherein R is:
  i) an ether having the formula —O[CH$_2$]$_k$R$^3$; or
  ii) an amine having the formula —NR$^{4a}$R$^{4b}$;
$R^3$ is substituted or unsubstituted aryl;
$R^{4a}$ and $R^{4b}$ are each independently:
  a) hydrogen; or
  b) —[C(R$^{5a}$R$^{5b}$)]$_x$R$^6$;
each $R^{5a}$ and $R^{5b}$ are independently hydrogen, —OR$^7$, —N(R$^7$)$_2$, —CO$_2$R$^7$, —CON(R$^7$)$_2$, $C_1$–$C_4$ linear, branched, or cyclic alkyl; $R^6$ is —OR$^7$, —N(R$^7$)$_2$, —CO$_2$R$^7$, —CON(R$^7$)$_2$; substituted or unsubstituted $C_1$–$C_4$ alkyl, substituted or unsubstituted aryl, or substituted or unsubstituted heteroaryl; $R^7$ is hydrogen, a water-soluble cation, $C_1$–$C_4$ alkyl, or substituted or unsubstituted aryl; the index x is from 0 to 5;
$R^1$ is selected from the group consisting of 4-fluorophenyl, 2,4-difluorophenyl, and 4-chlorophenyl;
each $R^{2a}$ or $R^{2b}$ unit is independently selected from the group consisting of:
  a) hydrogen;
  b) one $R^{2a}$ and one $R^{2b}$ are taken together to form a substituted or unsubstituted ring having from 4 to 8 atoms, said ring selected from the group consisting of:
    i) carbocyclic;
    ii) heterocyclic;
    iii) aryl;
    iv) heteroaryl;
    v) bicyclic; and
    vi) heterobicyclic;
  c) one $R^{2a}$ and one $R^{2b}$ are taken together to form a double bond;

d) —$(CH_2)_jNR^{9a}R^{9b}$; and e) —$(CH_2)_jCO_2R^{10}$;

j is 0.

10. A compound according to claim 9 wherein R is selected from the group consisting of phenoxy, 2-fluorophenoxy, 3-fluorophenoxy, 4-fluorophenoxy, 2,6-difluorophenoxy, 2-cyanophenoxy, 3-cyanophenoxy, 2-trifluoromethylphenoxy, 4-trifluoromethylphenoxy, 2-methylphenoxy, 4-methylphenoxy, 2,4-dimethylphenoxy, 3-N-acetylaminophenoxy, 2-methoxyphenoxy, 4-methoxyphenoxy, and 3-benzo[1,3]dioxol-5-yl.

11. A compound according to claim 9 wherein R is selected from the group consisting of 1-(S)-phenylethylamino, 1-(S)-(4-fluorophenyl)ethylamino, 1-(S)-(2-aminophenyl)ethylamino, 1-(S)-(2-methylphenyl)ethylamino, 1-(S)-(4-methylphenyl)ethylamino, 1-(S)-(4-methylphenyl)ethylamino, 1-(S)-(4-propanesulfonylphenyl)ethylamino, 1-(S)-(3-benzo[1,3]dioxol-5-yl)ethylamino, 1-(S)-(pyridin-2-yl)ethylamino, 1-(S)-(pyridin-3-yl)ethylamino, methylamino, ethylamino, propylamino, cyclopropylamine, cyclopropyl-methylamino, tert-butylamino, 1-(S)-(cyclopropyl)ethylamino, 1-(S)-(cyclopropylmethyl)-ethylamino, 1-(R)-(α)-(carboxy)benzylamino, and 1-(S)-(α)-(methyl)benzylamino.

12. A compound according to claim 1 having the formula:

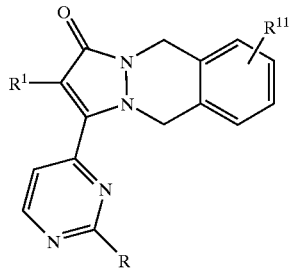

wherein R is:

i) an ether having the formula —$O[CH_2]_kR^3$; or ii) an amine having the formula —$NR^{4a}R^{4b}$;

$R^3$ is substituted or unsubstituted aryl;

$R^{4a}$ and $R^{4b}$ are each independently:

a) hydrogen; or b) —$[C(R^{5a}R^{5b})]_xR^6$;

each $R^{5a}$ and $R^{5b}$ are independently hydrogen, —$OR^7$, —$N(R^7)_2$, —$CO_2R^7$, —$CON(R^7)_2$; $C_1$–$C_4$ linear, branched, or cyclic; $R^6$ is hydrogen, —$OR^7$, —$N(R^7)_2$, —$CO_2R^7$, —$CON(R^7)_2$; substituted or unsubstituted $C_1$–$C_4$ alkyl, substituted or unsubstituted aryl, or substituted or unsubstituted heteroaryl; $R^7$ is hydrogen, a water-soluble cation, $C_1$–$C_4$ alkyl, or substituted or unsubstituted aryl; the index x is 0;

$R^1$ is selected from the group consisting of 4-fluorophenyl, 2,4-difluorophenyl, and 4-chlorophenyl;

each $R^{2a}$ or $R^{2b}$ unit is independently selected from the group consisting of:

a) hydrogen;

b) one $R^{2a}$ and one $R^{2b}$ are taken together to form a substituted or unsubstituted ring having from 4 to 8 atoms, said ring selected from the group consisting of:
i) carbocyclic;
ii) heterocyclic;
iii) aryl;
iv) heteroaryl;
v) bicyclic; and
vi) heterobicyclic;

c) one $R^{2a}$ and one $R^{2b}$ are taken together to form a double bond;

d) —$NR^{9a}R^{9b}$; and e) —$CO_2R^{10}$;

$R^{11}$ i) —$[C(R^{12})_2]_p(CH=CH)_qR^{12}$; wherein p is from 0 to 12; q is from 0 to 12;

ii) —$C(Z)R^{12}$;

iii) —$C(Z)_2R^{12}$;

iv) —$C(Z)CH=CH_2$;

v) —$C(Z)N(R^{12})_2$;

vi) —$C(Z)NR^{12}N(R^{12})_2$;

vii) —CN;

viii) —CNO;

ix) —$CF_3$, —$CCl_3$, —$CBr_3$;

Z) —$N(R^{12})_2$;

xi) —$NR^{12}CN$;

xii) —$NR^{12}C(Z)R^{12}$;

xiii) —$NR^{12}C(Z)N(R^{12})_2$;

xiv) —$NHN(R^{12})_2$;

xv) —$NHOR^{12}$;

xvi) —NCS;

xvii) —$NO_2$;

xviii) —$OR^{12}$;

xix) —OCN;

xx) —$OCF_3$, —$OCCl_3$, —$OCBr_3$;

xxi) —F, —Cl, —Br, —I, and mixtures thereof;

xxii) —SCN;

xxiii) —$SO_3M$;

xxiv) —$OSO_3M$;

xxv) —$SO_2N(R^{12})_2$;

xxvi) —$SO_2R^{12}$;

xxii) —$P(O)H_2$;

xxviii) —$PO_2$;

xxix) —$P(O)(OH)_2$;

wherein $R^{12}$ is hydrogen, substituted or unsubstituted $C_1$–$C_{20}$ linear, branched, or cyclic alkyl, $C_6$–$C_{20}$ aryl, $C_7$–$C_{20}$ alkylenearyl; M is hydrogen, or a salt forming cation; Z is =O, =S, =$NR^{12}$.

13. A compound according to claim 12 wherein R is selected from the group consisting of phenoxy, 2-fluorophenoxy, 3-fluorophenoxy, 4-fluorophenoxy, 2,6-difluorophenoxy, 2-cyanophenoxy, 3-cyanophenoxy, 2-trifluoromethylphenoxy, 4-trifluoromethylphenoxy, 2-methylphenoxy, 4-methylphenoxy, 2,4-dimethylphenoxy, 3-N-acetylaminophenoxy, 2-methoxyphenoxy, 4-methoxyphenoxy, and 3-benzo[1,3]dioxol-5-yl.

14. A compound according to claim 12 wherein R is selected from the group consisting of 1-(S)-phenylethylamino, 1-(S)-(4-fluorophenyl)ethylamino, 1-(S)-(2-aminophenyl)ethylamino, 1-(S)-(2-methylphenyl)ethylamino, 1-(S)-(4-methylphenyl)ethylamino, 1-(S)-(4-methylphenyl)ethylamino, 1-(S)-(4-propanesulfonylphenyl)ethylamino, 1-(S)-(3-benzo[1,3]dioxol-5-yl)ethylamino, 1-(S)-(pyridin-2-yl)ethylamino, 1-(S)-(pyridin-3-yl)ethylamino, methylamino, ethylamino, propylamino, cyclopropylamine, cyclopropyl-methylamino, tert-butylamino, 1-(S)-(cyclopropyl)ethylamino, 1-(S)-

(cyclopropylmethyl)-ethylamino, 1-(R)-(α)-(carboxy) benzylamino, and 1-(S)-(α)-(methyl)benzylamino.

15. A compound according to claim 1 having the formula:

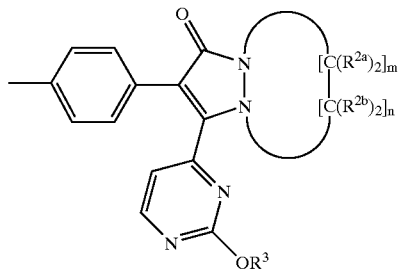

wherein each $R^{2a}$ or $R^{2b}$ unit is independently selected from the group consisting of:
a) hydrogen;
b) one $R^{2a}$ and one $R^{2b}$ are taken together to form a substituted or unsubstituted ring having from 4 to 8 atoms, said ring selected from the group consisting of:
   i) carbocyclic;
   ii) heterocyclic; and
   iii) aryl;
c) one $R^{2a}$ and one $R^{2b}$ are taken together to form a double bond;
d) —$NR^{9a}R^{9b}$; and
e) —$CO_2R^{10}$;
$R^3$ is substituted or unsubstituted aryl.

16. A compound according to claim 15 wherein $R^3$ is selected from the group consisting of phenyl, 2-fluorophenyl, 3-fluorophenyl, 4-fluorophenyl, 2,6-difluorophenyl, 2-cyanophenyl, 3-cyanophenyl, 2-trifluoromethylphenyl, 4-trifluoromethylphenyl, 2-methylphenyl, 4-methylphenyl, 2,4-dimethylphenyl, 3-N-acetylaminophenyl, 2-methoxyphenyl, 4-methoxyphenyl, and 3-benzo[1,3]dioxol-5-yl.

17. A compound according to claim 1 having the formula:

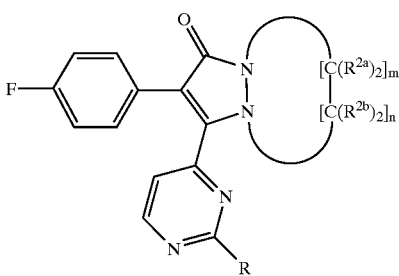

wherein R has the formula:

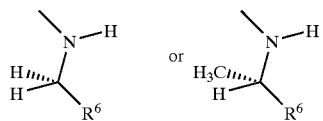

$R^6$ is selected from the group consisting of phenyl, 4-fluorophenyl, 2-aminophenyl, 2-methylphenyl, 4-methylphenyl, 4-methoxyphenyl, 4-(propanesulfonyl)phenyl, 3-benzo[1,3]dioxol-5-yl, pyridin-2-yl, pyridin-3-yl, methyl, ethyl, vinyl, cyclopropyl, cyclohexyl, methoxymethyl, methoxyethyl, 1-hydroxy-1-methylethyl, and —$CO_2H$;

each $R^{2a}$ or $R^{2b}$ unit is independently selected from the group consisting of:
a) hydrogen;
b) one $R^{2a}$ and one $R^{2b}$ are taken together to form a substituted or unsubstituted ring having from 4 to 8 atoms, said ring selected from the group consisting of:
   i) carbocyclic;
   ii) heterocyclic; and
   iii) aryl;
c) one $R^{2a}$ and one $R^{2b}$ are taken together to form a double bond;
d) —$NR^{9a}R^{9b}$; and
e) —$CO_2R^{10}$.

18. A compound according to claim 17 wherein one $R^{2a}$ and one $R^{2b}$ are taken together to form a substituted or unsubstituted aryl ring.

19. A composition comprising:
a) an effective amount of one or more compounds, including all enantiomeric and diasteriomeric forms and pharmaceutically acceptable salts thereof, said compound having the formula:

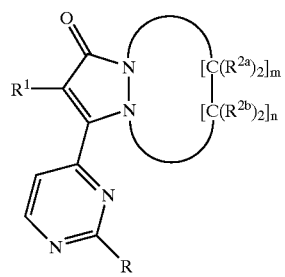

wherein R is:
a) hydrogen;
b) —$O[CH_2]_kR^3$; or
c) —$NR^{4a}R^{4b}$;
$R^3$ is substituted or unsubstituted $C_1$–$C_4$ alkyl, substituted or unsubstituted hydrocarbyl, substituted or unsubstituted heterocyclyl, substituted or unsubstituted aryl or alkylenearyl, substituted or unsubstituted heteroaryl or alkyleneheteroaryl; the index k is from 0 to 5;
$R^{4a}$ and $R^{4b}$ are each independently:
a) hydrogen; or
b) —$[C(R^{5a}R^{5b})]_kR^6$;
each $R^{5a}$ and $R^{5b}$ are independently hydrogen, —$OR^7$, —$N(R^7)_2$, —$CO_2R^7$, —$CON(R^7)_2$; $C_1$–$C_4$ linear, branched, or cyclic alkyl; $R^6$ is hydrogen, —$OR^7$, —$N(R^7)_2$, —$CO_2R^7$, —$CON(R^7)_2$; substituted or unsubstituted $C_1$–$C_4$ alkyl, substituted or unsubstituted aryl, or substituted or unsubstituted heteroaryl; $R^7$ is hydrogen, a water-soluble cation, $C_1$–$C_4$ alkyl, or substituted or unsubstituted aryl; the index x is from 0 to 5;
$R^1$ is:
a) substituted or unsubstituted aryl; or
b) substituted or unsubstituted heteroaryl;
$R^{2a}$ and $R^{2b}$ units are each independently selected from the group consisting of:
a) hydrogen;
b) —$O(CH_2)_jR^8$;
c) —$(CH_2)_jNR^{9a}R^{9b}$;
d) —$(CH_2)_jCO_2R^{10}$;
e) —$(CH_2)_jOCO_2R^{10}$
f) —$(CH_2)_jCON(R^{10})_2$;

g) two $R^{2a}$ or two $R^{2b}$ units from the same carbon atom can be taken together to form a carbonyl unit;

h) one $R^{2a}$ and one $R^{2b}$ are taken together to form a substituted or unsubstituted ring comprising from 4 to 8 atoms, said ring selected from the group consisting of:
  i) carbocyclic;
  ii) heterocyclic;
  iii) aryl;
  iv) heteroaryl;
  v) bicyclic; and
  vi) heterobicyclic;
i) and mixtures thereof;

$R^8$, $R^{9a}$, $R^{9b}$, and $R^{10}$ are each independently hydrogen, $C_1$–$C_4$ alkyl; or $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5; m is an index from 1 to 5, n is an index from 1 to 5; m+n=from 2 to 6, with the provision that m+n is not 3; and b) one or more pharmaceutically acceptable excipients.

20. A method for treating osteoarthritis or rheumatoid arthritis, said method comprising the step of administering to a human or higher mammal a composition comprising:
a) an effective amount of one or more compounds, including all enantiomeric and diasteriomeric forms and pharmaceutically acceptable salts thereof, said compound having the formula:

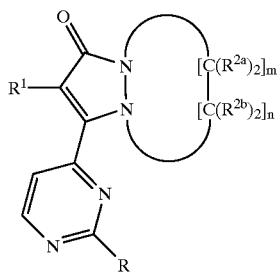

wherein R is:
a) hydrogen:
b) —O[CH$_2$]$_k$R$^3$; or
c) —NR$^{4a}$R$^{4b}$;

$R^3$ is substituted or unsubstituted $C_1$–$C_4$ alkyl, substituted or unsubstituted hydrocarbyl, substituted or unsubstituted heterocyclyl, substituted or unsubstituted aryl or alkylenearyl, substituted or unsubstituted heteroaryl or alkyleneheteroaryl; the index k is from 0 to 5;

$R^{4a}$ and $R^{4b}$ are each independently:
a) hydrogen; or
b) —[C(R$^{5a}$R$^{5b}$)]$_x$R$^6$;

each $R^{5a}$ and $R^{5b}$ are independently hydrogen, —OR$^7$, —N(R$^7$)$_2$, —CO$_2$R$^7$, —CON(R$^7$)$_2$; $C_1$–$C_4$ linear, branched, or cyclic alkyl; $R^6$ is hydrogen, —OR$^7$, —N(R$^7$)$_2$, —CO$_2$R$^7$, —CON(R$^7$)$_2$; substituted or unsubstituted $C_1$–$C_4$ alkyl, substituted or unsubstituted aryl, or substituted or unsubstituted heteroaryl; $R^7$ is hydrogen, a water-soluble cation, $C_1$–$C_4$ alkyl, or substituted or unsubstituted aryl; the index x is from 0 to 5;

$R^1$ is:
a) substituted or unsubstituted aryl; or
b) substituted or unsubstituted heteroaryl;

$R^{2a}$ and $R^{2b}$ units are each independently selected from the group consisting of:
a) hydrogen;
b) —O(CH$_2$)$_j$R$^8$;
c) —(CH$_2$)$_j$N R$^{9a}$R$^{9b}$;
d) —(CH$_2$)$_j$CO$_2$R$^{10}$;
e) —(CH$_2$)$_j$OCO$_2$R$^{10}$
f) —(CH$_2$)$_j$CON(R$^{10}$)$_2$;
g) two $R^{2a}$ or two $R^{2b}$ units from the same carbon atom can be taken together to form a carbonyl unit;

h) one $R^{2a}$ and one $R^{2b}$ are taken together to form a substituted or unsubstituted ring comprising from 4 to 8 atoms, said ring selected from the group consisting of:
  i) carbocyclic;
  ii) heterocyclic;
  iii) aryl;
  iv) heteroaryl;
  v) bicyclic; and
  vi) heterobicyclic;
i) and mixtures thereof;

$R^8$, $R^{9a}$, $R^{9b}$, and $R^{10}$ are each independently hydrogen, $C_1$–$C_4$ alkyl; or $R^{9a}$ and $R^{9b}$ can be taken together to form a carbocyclic or heterocyclic ring comprising from 3 to 7 atoms; two $R^{10}$ units can be take together to form a carbocyclic or heterocyclic ring comprising from 3 to 7 atoms; j is an index from 0 to 5; m is an index from 1 to 5, n is an index from 1 to 5; m+n=from 2 to 6, with the provision that m+n is not 3; and b) one or more pharmaceutically acceptable excipients.

* * * * *